United States Patent [19]
Roberts et al.

[11] Patent Number: 5,219,863
[45] Date of Patent: Jun. 15, 1993

[54] ANGIOTENSIN II ANTAGONIZING COMPOUNDS CONTAINING A 1,5-NAPHTHYRIDINE OR A QUINOLINE MOIETY

[75] Inventors: David A. Roberts, Congleton; Robert J. Pearce; Robert H. Bradbury, both of Wilmslow, all of England

[73] Assignee: Imperial Chemical Industires PLC, London, England

[21] Appl. No.: 791,717

[22] Filed: Nov. 14, 1991

[30] Foreign Application Priority Data

Nov. 19, 1990 [GB] United Kingdom ............... 9025123

[51] Int. Cl.$^5$ .................. A61K 31/435; A61K 31/47; C07D 471/04; C07D 215/233
[52] U.S. Cl. .................... 514/300; 514/312; 546/122; 546/123; 546/153
[58] Field of Search ............ 546/153, 122, 123; 514/300, 312

[56] References Cited

U.S. PATENT DOCUMENTS

| | | | |
|---|---|---|---|
| 4,576,953 | 3/1986 | Le Count | 514/312 |
| 4,607,040 | 8/1986 | Pearce et al. | 514/312 |
| 4,820,843 | 4/1989 | Aldrich et al. | 548/252 |
| 4,880,804 | 11/1989 | Carini et al. | 514/234.5 |
| 4,920,131 | 4/1990 | Huang et al. | 514/311 |
| 5,126,344 | 6/1992 | Roberts et al. | 546/122 |

FOREIGN PATENT DOCUMENTS

| | | |
|---|---|---|
| 0253310 | 1/1988 | European Pat. Off. . |
| 0315399 | 5/1989 | European Pat. Off. . |
| 0323841 | 7/1989 | European Pat. Off. . |
| 0326328 | 8/1989 | European Pat. Off. . |
| 412848 | 2/1991 | European Pat. Off. . |
| WO89/04304 | 5/1989 | PCT Int'l Appl. . |
| 91/07404 | 5/1991 | PCT Int'l Appl. . |

OTHER PUBLICATIONS

G. R. Proctor, et al. *J. Chem. Soc., Perkin Trans. I* (1972) (14), 1803–1808.
M. I. Husain, et al. *J. Chem. Soc. Pak.* (1986) 8(3), 335–339.
Youssefyeh, R. D., et al. (principal author Huang) *J. Med. Chem.* (1990), 33, 1186–1194; *Chem. Abstr.* (1990), 112, 17, Abstract 131,890u.
Huang, F—C *J. Med. Chem.* (1990), 33, 1194–1200.

*Primary Examiner*—Bernard Dentz
*Attorney, Agent, or Firm*—Thomas E. Jackson

[57] ABSTRACT

The invention concerns pharmaceutically useful novel compounds of the formula I, in which $R^1$, $R^2$, $R^3$, $R^4$, $R^5$, $X$, $X^1$ and $Z$ have the various meanings defined herein, and their non-toxic salts, and pharmaceutical compositions containing them. The novel compounds are of value in treating conditions such as hypertension and congestive heart failure. The invention further concerns processes for the manufacture of the novel compounds and the use of the compounds in medical treatment.

13 Claims, No Drawings

ANGIOTENSIN II ANTAGONIZING COMPOUNDS CONTAINING A 1,5-NAPHTHYRIDINE OR A QUINOLINE MOIETY

This invention concerns novel nitrogen compounds and, more particularly, novel quinoline and 1,5-naphthyridine derivatives which possess pharmacologically useful properties in antagonising, at least in part, one or more of the actions of the substances known as angiotensins, and in particular of that known as angiotensin II (hereafter referred to as AII). The invention also concerns pharmaceutical compositions of the novel compounds for use in treating diseases or medical conditions such as hypertension, congestive heart failure and/or hyperaldosteronism in warm-blooded animals (including man), as well as in other diseases or medical conditions in which the renin-angiotensin-aldosterone system plays a significant causative role. The invention also includes processes for the manufacture of the novel compounds and their use in treating one of the aforementioned diseases or medical conditions and for the production of novel pharmaceuticals for use in such medical treatments.

The angiotensins are key mediators of the renin-angiotensin-aldosterone system, which is involved in the control of homeostasis and fluid/electrolyte balance in many warm-blooded animals, including man. The angiotensin known as AII is produced by the action of angiotensin converting enzyme (ACE) on angiotensin I, itself produced by the action of the enzyme renin on the blood plasma protein angiotensinogen. AII is a potent spasmogen especially in the vasculature and is known to increase vascular resistance and blood pressure. In addition, the angiotensins are known to stimulate the release of aldosterone and hence result in vascular congestion and hypertension via sodium and fluid retention mechanisms. Hitherto there have been a number of different approaches to pharmacological intervention in the renin-angiotensin-aldosterone system for therapeutic control of blood pressure and/or fluid/electrolyte balance, including, for example, inhibiting the actions of renin or ACE. However, there remains a continuing need for an alternative approach because of the side-effects and/or idiosyncratic reactions associated with any particular therapeutic approach.

Certain structurally-related substituted quinolines and naphthyridines having AII antagonist activity are disclosed in our copending European Patent Application, Publication No. 412848 and International Patent Application No. PCT/GB90/01776 respectively.

We have now discovered that the compounds of the invention (set out below) surprisingly antagonise one or more of the actions of the substances known as angiotensins (and in particular of AII) and thus minimise the physiological effects associated with their presence in warm-blooded animals (including man) and this is the basis of the invention.

According to the invention there is provided a compound of the formula I (set out hereinafter, together with the other chemical formulae identified by Roman numerals) wherein:

$R^1$ is hydrogen, (1–8C)alkyl, (3–8C)cycloalkyl, (3–8C)cycloalkyl(1–4C)alkyl, phenyl, phenyl(1–4C)alkyl or (1–4C)alkyl bearing one or more fluoro substituents;

$R^2$ is hydrogen or (1–4C)alkyl;

$R^3$ is phenyloxy, pyridyloxy or a group of the formula —Y.A.B wherein Y is an oxygen or sulphur atom; A is (1–6C)alkylene, (3–6C)alkenylene or a 1,3-cyclopentylene or 1,4-cyclohexylene moiety, the latter two groups optionally bearing 1 or 2 (1–4C)alkyl groups; and B is selected from hydroxy, (1–4C)alkoxy, phenyl, phenyloxy, phenyl(1–4C)alkoxy, pyridyl(1–4C)alkoxy, 4-morpholino(1–4C)alkoxy, phenylamino, amino, alkylamino and dialkylamino of up to 6 carbon atoms, (1–4C)alkanoylamino, (1–4C)alkylsulphonylamino, phenylsulphonylamino, sulphamoylamino (—NH.SO$_2$.NH$_2$), carboxamidomethylamino (—NH.CH$_2$.CO.NH$_2$), (1–4C)alkanoyloxy, phenylcarbonyloxy, aminocarbonyloxy (—O.CO.NH$_2$), (1–4C)alkylaminocarbonyloxy, carboxy, (1–4C)alkoxycarbonyl, carbamoyl, N-alkylcarbamoyl and di-(N-alkyl)carbamoyl of up to 7 carbon atoms, (1–4C)alkanoyl, 4-morpholino, 1-imidazolyl, succinimido, thiazolyl and thiadiazolyl; or B is a group of the formula —Y$^1$.B$^1$. wherein Y$^1$ is oxy, oxycarbonyl or imino and B$^1$ is a 5 or 6-membered saturated or unsaturated heterocyclic ring containing 1 or 2 nitrogen atoms and linked to Y$^1$ by a ring carbon atom; or Y$^1$ is oxycarbonyl and B$^1$ is a 4-morpholino group or a 5 or 6-membered saturated heterocyclic ring containing 1 or 2 nitrogen atoms, optionally bearing a (1–4C)alkyl group and linked to Y$^1$ by a ring nitrogen atom; and wherein in B$^1$ the remainder of the ring atoms are carbon;

$R^4$ is selected from hydrogen, (1–4C)alkyl, (1–4C)alkoxy, fluoro(1–4C)alkoxy, halogeno, trifluoromethyl, cyano, nitro, hydroxy, amino, alkylamino and dialkylamino of up to 6 carbon atoms, carboxy, (1–4C)alkoxycarbonyl, carbamoyl and N-alkylcarbamoyl and di-(N-alkyl)carbamoyl of up to 7 carbon atoms;

$R^5$ is hydrogen, (1–4C)alkyl, (1–4C)alkoxy, halogeno, trifluoromethyl, cyano or nitro;

X is phenylene optionally bearing a substituent selected from (1–4C)alkyl, (1–4C)alkoxy, halogeno, trifluoromethyl, cyano and nitro, or X is a direct bond between the adjacent phenyl and methylene groups;

$X^1$ is a methine (—CH=) group or a nitrogen atom; and

Z is 1H-tetrazol-5-yl, —CO.NH.(1H-tetrazol-5-yl) or a group of the formula —CO.OR$^6$ or —CO.NH.SO$_2$.R$^7$ in which R$^6$ is hydrogen or a non-toxic, biodegradable residue of a physiologically acceptable alcohol or phenol, and R$^7$ is (1–6C)alkyl, (3–8C)cycloalkyl or phenyl; and wherein any of said phenyl moieties may be unsubstituted or bear one or two substituents independently selected from (1–4C)alkyl, (1–4C)alkoxy, halogeno, cyano and trifluoromethyl; or a physiologically acceptable salt thereof.

It will be appreciated that, depending on the nature of the substituents, certain of the formula I compounds may possess one or more chiral centres and may be isolated in one or more racemic or optically active forms. It is to be understood that this invention concerns any form of such a compound of formula I which possesses the afore-mentioned useful pharmacological properties, it being well known how to make optically active forms, for example by synthesis from suitable chiral intermediates, and how to determine their pharmacological properties, for example by use of the standard tests described hereinafter.

It is to be understood that generic terms such as "alkyl" include both straight and branched chain variants when the carbon numbers permit. However, when a particular radical such as "propyl" is given, it is specific to the straight chain variant, branched chain variants such as "isopropyl" being specifically named where intended. The same convention applies to other radicals.

A particular value for $R^1$ when it is alkyl is, for example, methyl, ethyl, propyl, butyl, isobutyl, sec-butyl, pentyl or hexyl; when it is cycloalkyl is, for example, cyclopropyl, cyclopentyl or cyclohexyl; when it is cycloalkyl-alkyl is, for example, cyclopropylmethyl, cyclopentylmethyl, cyclohexylmethyl or 2-cyclopentylethyl; when it is phenylalkyl is, for example, benzyl, 1-phenylethyl or 2-phenylethyl; and when it is alkyl bearing one or more fluoro substituents is, for example, fluoromethyl, trifluoromethyl, 2,2,2-trifluoroethyl or pentafluoroethyl.

A particular value for $R^2$ when it is alkyl is, for example, methyl or ethyl.

A particular value for A when it is (1–6C)alkylene is, for example, methylene, ethylene, trimethylene or tetramethylene, in any of which one methylene may bear 1 or 2 methyl substituents; and when it is (3–6C)alkenylene is, for example, $-CH_2.CH=CH-$ or $-CH_2.CH=CH.CH_2-$.

Particular values for B, $R^4$, $R^5$ or for an optional substituent which may be present when X is phenylene, include, by way of example: for alkyl, methyl and ethyl; for alkoxy, methoxy, ethoxy and isopropoxy; for fluoroalkoxy: trifluoromethoxy, 2-fluoroethoxy, 2,2,2-trifluoroethoxy and 3,3,3-trifluoropropoxy; for halogeno, fluoro, chloro, bromo and iodo; for alkylamino: methylamino, ethylamino and butylamino; for dialkylamino: dimethylamino, diethylamino and dipropylamino; for N-alkylcarbamoyl: N-methyl and N-ethylcarbamoyl; for di(N-alkyl)carbamoyl: N,N-dimethylcarbamoyl and N,N-diethylcarbamoyl; for alkoxycarbonyl: methoxycarbonyl, ethoxycarbonyl and propoxycarbonyl; for phenylalkoxy, benzyloxy and phenethyloxy; for pyridylalkoxy, 2-pyridylmethoxy, 3-pyridylmethoxy, 4-pyridylmethoxy and 3-pyridylethoxy; for 4-morpholinoalkoxy, 4-morpholinomethoxy and 4-morpholinoethoxy; for alkanoylamino, formamido, acetamido and propionylamido; for alkylsulphonylamino, methylsulphonylamino and ethylsulphonylamino; for alkanoyloxy, acetyloxy and propionyloxy; for alkylaminocarbonyloxy, methylaminocarbonyloxy and ethylaminocarbonyloxy; and for alkanoyl, formyl, acetyl and propionyl.

A particular value for B when it is thiazolyl is, for example, thiazol-4-yl and when it is thiadiazolyl is, for example, 1,2,5-thiadiazolyl.

A particular value for $B^1$ when it is a 5 or 6-membered unsaturated heterocyclic ring containing 1 or 2 nitrogen atoms is, for example, pyrrolyl, imidazolyl, pyrazolyl, pyridyl, pyrazinyl, pyrimidinyl or pyridazinyl; and when it is a 5 or 6-membered saturated heterocyclic ring containing 1 or 2 nitrogen atoms is, for example, pyrrolidinyl, imidazolidinyl, pyrazolinyl, piperidinyl or piperazinyl.

A particular value for an alkyl group which may be present on A when it is a 1,3-cyclopentylene or 1,4-cyclohexylene moiety or on $B^1$ when it a 5 or 6-membered saturated heterocyclic ring is, for example, methyl or ethyl.

A particular value for $R^6$ when it is a non-toxic, biodegradable residue of a physiologically acceptable alcohol or phenol is, for example, a residue derived from a (1–6C)alkanol such as methanol or ethanol, or phenol, glycerol or the like.

A particular value for $R^7$ when it is alkyl is, for example, methyl, ethyl, propyl, isopropyl, butyl or pentyl; and when it is cycloalkyl is, for example, cyclobutyl, cyclopentyl or cyclohexyl.

Particular values for optional substituents which may be present on phenyl moieties include, by way of example, for halogeno, fluoro, chloro and bromo; for alkyl, methyl or ethyl; and for alkoxy, methoxy and ethoxy.

A specific value for X which is of particular interest is, for example, p-phenylene.

A preferred value for $R^2$, $R^4$, $R^5$ or $R^6$ is, for example, hydrogen and for $R^1$ is, for example, methyl or ethyl.

A preferred value for Y is, for example, oxygen; for A is, for example, ethylene; and for B is, for example, hydroxy.

A preferred value for $R^3$ is, for example, 2-hydroxyethoxy.

A preferred value for $X^1$ is, for example, a nitrogen atom.

A preferred value for Z is, for example, carboxy or 1H-tetrazol-5-yl, which latter is especially preferred and, in particular, when it is attached ortho to the group X.

A group of compounds of the invention which is of special interest comprises those compounds of the formula Ia wherein $R^1$, $R^2$, $R^3$, $R^4$, $R^5$, X and Z have any of the meanings defined above, and the physiologically acceptable salts thereof. Preferably, within this group, X is, for example, p-phenylene and Z is, for example, 1H-tetrazol-5-yl, and particularly when the groups X and Z are situated ortho to each other.

A particularly preferred group of compounds of the invention comprises those compounds of formula Ia wherein $R^3$ is a group of the formula —Y.A.B wherein Y is oxygen, A is (1–6C)alkylene, B is hydroxy, X is p-phenylene, Z is 1H-tetrazol-5-yl and $R^1$, $R^2$, $R^4$ and $R^5$ have any of the meanings defined above, and the pharmaceutically acceptable salts thereof.

Compounds of the invention which are of particular interest include, for example, the compounds of formula I described hereinafter in the accompanying Examples 1, 2, 4, 5, 8, 9, 12, 15 and 19 and these compounds, or a physiologically acceptable salt thereof, are provided as a further feature of the invention.

Although all of the formula I compounds can form salts with suitable acids, it will be appreciated that the compounds of formula I wherein Z is other than an ester group or wherein $R^3$ or $R^4$ is or bears an acidic group, for example, a carboxy group, can also form salts with bases as well as with acids. Particularly suitable salts for such compounds therefore include, for example, salts with bases affording physiologically acceptable cations, for example, alkali metal (such as sodium and potassium), alkaline earth metal (such as magnesium and calcium), aluminium and ammonium salts, as well as salts with suitable organic bases, such as with ethanolamine, methylamine, diethylamine or triethylamine, as well as salts with acids forming physiologically acceptable anions, such as salts with mineral acids, for example with hydrogen halides (such as hydrogen chloride and hydrogen bromide), sulphuric and phosphoric acid, and with organic acids, for example with p-toluenesulphonic, methanesulphonic, citric, tartaric and oxalic acids.

The compounds of formula I may be obtained by standard procedures of organic chemistry well known in the art for the production of structurally analogous compounds. Such procedures are provided as a further feature of the invention and include, by way of example, the following procedures in which the generic radicals have any of the values given above, unless stated otherwise:

a) For those compounds in which Z is carboxy (that is in which Z is a group of the formula —CO.OR$^6$ in which R$^6$ is hydrogen), a carboxylic acid derivative of the formula II, in which Q is a protected carboxy group selected from (1-6C)alkoxycarbonyl (especially methoxy-, ethoxy-, propoxy- or t-butoxy-carbonyl), phenoxycarbonyl, benzyloxycarbonyl and carbamoyl, is converted to carboxy.

The conversion may be carried out, for example by hydrolysis, conveniently in the presence of a suitable base such as an alkali metal hydroxide, for example, lithium, sodium or potassium hydroxide. The hydrolysis is generally carried out in the presence of a suitable aqueous solvent or diluent, for example in an aqueous (1-4C)alkanol, such as aqueous methanol or ethanol. However, it may also be performed in a mixture of an aqueous and non-aqueous solvent such as water and toluene using a conventional quaternary ammonium phase transfer catalyst. The hydrolysis is generally performed at a temperature in the range, for example, 0°-120° C. depending on the reactivity of the group Q. In general, when Q is carbamoyl, temperatures in the range, for example, 40°-120° C. are required to effect the hydrolysis.

Alternatively, when Q is benzyloxycarbonyl, the conversion may also be performed by hydrogenolysis, for example using hydrogen at 1-3 bar in the presence of a suitable catalyst, such as palladium on charcoal or on calcium sulphate, in a suitable solvent or diluent such as an (1-4C)alkanol (typically ethanol or 2-propanol) and at a temperature in the range, for example, 0°-40° C.

Further, when Q is t-butoxycarbonyl, the conversion may also be carried out by hydrolysis at a temperature in the range, for example, 0°-100° C., in the presence of a strong acid catalyst, such as trifluoroacetic acid. The hydrolysis may either be performed in an excess of the acid or in the presence of a suitable diluent such as tetrahydrofuran, t-butyl methyl ether or 1,2-dimethoxyethane.

b) For those compounds of formula I wherein Z is tetrazolyl, a compound of the formula III in which L is a suitable protecting group, such as trityl, benzhydryl, trialkyl tin (for example trimethyltin) or triphenyltin, affixed to a nitrogen of the tetrazolyl moiety, is deprotected.

The reaction conditions used to carry out the deprotection necessarily depend on the nature of the group L. As an illustration, when it is trityl, benzhydryl, trialkyl tin or triphenyltin, the decomposition conditions include, for example, acid catalysed hydrolysis in a mineral acid (such as aqueous hydrochloric acid), conveniently in an aqueous solvent (such as aqueous methanol, ethanol or 2-propanol). Alternatively, a trityl or benzhydryl group may be removed by hydrogenolysis, for example as described in (a) above for conversion of a benzyloxycarbonyl to a carboxy.

Compounds of the formula III wherein L is trialkyltin or triphenyltin may be obtained, for example, by reaction of a nitrile of the formula IX with a trialkyltin azide or triphenyltin azide respectively. The reaction is conveniently carried out in a suitable solvent or diluent, such as toluene or xylene, and at a temperature in the range, for example, 50°-150° C. The nitriles of the formula IX may be obtained, for example, by reaction of a compound of the formula VII wherein P$^1$ is a suitable leaving group, such as chloro, bromo, iodo, methanesulphonyloxy or p-toluenesulphonyloxy, with an alcohol of the formula XI, using similar conditions to those used in process (d) described hereinafter. Alternatively, the nitriles of the formula IX may be obtained from stepwise conversion of a compound of formula I wherein Z is a group of the formula —CO.OR$^6$ under standard conditions. The alcohols of formula XI may be obtained, for example, by standard procedures such as that illustrated in Scheme 1 for compounds in which X is phenylene. Nitriles of the formula IX in which X is phenylene may also be obtained, for example, by bromination of a suitably substituted 4'-methyl-biphenylcarbonitrile to the corresponding bromomethyl derivative followed by alkylation of a compound of formula IV in a similar manner to that described in process (c) described hereinafter.

Alternatively, compounds of the formula III may be obtained, for example, by reaction of a compound of the formula VII wherein P$^1$ is a suitable leaving group (such as halogeno, typically fluoro, chloro or bromo) with an alcohol of the formula XII under similar conditions to those described in process (d) hereinafter. The alcohols of formula XII may be obtained, for example, from the appropriate bromomethyl compound by standard procedures such as those shown in Scheme 1. It will be appreciated that other well known reagents and conditions may be used for carrying out the steps of Scheme 1 and may be dependent on the nature of the protecting group present on the tetrazole ring. For example, conventional hydrolytic conditions may be used for step (f) of Scheme 1 instead of reductive conditions.

It will be appreciated that compounds of the formula III may also be obtained by subsequent modification of a functional group present in another compound of the formula III previously prepared as described herein. For example, the hydroxy group present in a compound of the formula III wherein R$^3$ is a group of the formula —Y.A.B in which Y is oxygen, A is alkylene and B is hydroxy, obtained for example as illustrated in Scheme 2 and the accompanying examples, may be converted to an alkanoyloxy, phenylcarbonyloxy, alkylaminocarbonyloxy, alkoxy, phenylalkoxy, pyridylalkoxy or morpholinoalkoxy group by reaction with the appropriate alkyl or acyl halide or alkyl isocyanate using standard conditions of organic chemistry well known in the art. In addition, an ester group present in R$^3$ may be converted in, for example, an ethereal solvent to the corresponding tertiary alcohol with, for example, an alkylmagnesium halide or to the corresponding primary alcohol by reduction with, for example, lithium aluminium hydride.

c) A compound of the formula IV wherein R$^1$ is other than hydrogen is alkylated with a compound of the formula V wherein Hal. stands for a suitable leaving group such as chloro, bromo, iodo, methanesulphonyloxy or p-toluenesulphonyloxy.

The reaction is generally carried out in the presence of a suitable base, for example, an alkali metal alkoxide such as sodium methoxide or sodium ethoxide, an alkali metal hydride such as sodium hydride, an alkali metal carbonate such as sodium or potassium carbonate or an organic base such as diisopropylethylamine and in a suitable solvent or diluent, for example, a (1-4C)alkanol such as methanol or ethanol when an alkali metal alkoxide is used, or in a polar solvent such as N,N-dimethylformamide and at a temperature in the range, for example, 10°–100° C. Alternatively, a quaternary ammonium hydroxide may be used in a mixture of an aqueous and non-aqueous solvent such as water and dichloromethane. In carrying out process (c), when in the starting material Z is an acidic group, about two molecular equivalents of a suitable base is generally required, whereas when Z is a non-acidic group the presence of one molecular equivalent of a suitable base is generally sufficient.

Procedure (c) is particularly suitable for the production of those compounds of the formula I in which Z is a group of the formula —CO.OR$^6$ in which R$^6$ is other than hydrogen, for example wherein R$^6$ is (1–6C)alkyl, benzyl or phenyl, which compounds are also starting materials of formula II for the reaction described in (a) above. Similarly, using an analogous procedure, but starting with the appropriate halomethyl tetrazolyl derivative of the formula VI, the starting materials of the formula III may be obtained for procedure (b).

The compounds of formula IV wherein X$^1$ is a methine group may be obtained, for example, from the appropriately substituted aniline using similar procedures to those described in *Org. Syn.* 1953, Coll. Vol. III, pages 374 and 593 for the preparation of analogous compounds. The anilines may be obtained by analogy with procedures well known in the art, such as by O- or S-alkylation of an appropriate 4-aminophenol or 4-aminothiophenol with a compound of the formula P$^2$.A.B. wherein P$^2$ stands for a suitable leaving group such as chloro, bromo, iodo, methanesulphonyloxy or p-toluenesulphonyloxy, or of an appropriate 4-nitrophenol or 4-nitrothiophenol under similar conditions followed by reduction of the nitro group. Compounds of the formula IV wherein X$^1$ is a nitrogen atom may be obtained from the appropriately substituted 3-aminopyridine using an analogous procedure to that illustrated in Scheme 2, step (iii). The 3-aminopyridines may be obtained by reaction of a 2-halogeno-5-nitropyridine under basic conditions with a compound of the formula HO.A.B. or HS.A.B (which compounds are known or can be obtained by standard procedures of organic chemistry), followed by reduction of the nitro group. The necessary compounds of the formula V (and also of formula VI) may be made by standard procedures such as those which are illustrated in Scheme 1 for compounds in which X is phenylene.

Compounds of the formula VI wherein X is phenylene may also be conveniently obtained by reaction of a Grignard reagent, formed from a suitably substituted 4-bromotoluene, with a trialkyltin halide, such as tributyltin chloride, followed by reaction of the resulting (substituted)phenyltrialkyltin compound with a bromobenzonitrile in the presence of a palladium(O) catalyst, such as tetrakis(triphenylphosphine)palladium, and azo(bisisobutyronitrile). The resultant substituted 4'-methyl-biphenylcarbonitrile may then be converted to a compound of the formula VI by carrying out steps (b), (c) and (d) in a similar manner to that shown in Scheme 1. Alternatively, suitably substituted 4'-methylbiphenyl-carbonitriles may be obtained by reaction of 4-methylphenylboronic acid with an appropriately substituted bromobenzonitrile in the presence of a suitable palladium catalyst, such as palladium (II)chloride or tetrakis(triphenylphosphine)palladium, and azo(-bisisobutyronitrile).

(d) A compound of the formula VII wherein P$^1$ is a suitable leaving group (such as chloro, bromo, iodo, methanesulphonyloxy or p-toluenesulphonyloxy) is reacted with an alcohol of the formula VIII.

The reaction is generally carried out in the presence of a suitable base, for example an alkali metal alkoxide such as sodium methoxide or ethoxide or an alkali metal hydride such as sodium hydride and in a suitable solvent or diluent, for example a (1–4C)alkanol such as methanol or ethanol when an alkali metal alkoxide is used, or a polar solvent such as N,N-dimethylformamide. Alternatively, an alcohol of the formula VIII may be used in the form of its preformed alkali metal salt (when Z is a non-acidic group) or di-alkali metal salt (when Z is an acidic group). The reaction is usually performed at a temperature in the range of 40° to 120° C. The reaction may in preference be carried out with a formula VIII compound in the presence of an acid catalyst such as p-toluenesulphonic acid, instead of under basic conditions, and in the presence of an inert solvent or diluent such as toluene.

The compounds of the formula VII may be obtained, for example, by halogenation of the corresponding compound of formula IV, for example, by reaction with phosphorus oxychloride in the absence of a solvent, or in the presence of an inert solvent or diluent such as toluene or dioxane, and at a temperature in the range 60°–110° C. The alcohols of the formula VIII are known or can be prepared by standard procedures well known in the art.

(e) A compound of the formula XIII is reacted with a compound of the formula P$^2$.A.B wherein P$^2$ stands for a suitable leaving group such as chloro, bromo, iodo, methanesulphonyloxy or p-toluenesulphonyloxy.

The reaction is generally carried out in the presence of a suitable base, in a suitable solvent and under similar conditions to those described in process (d).

The compounds of the formula XIII wherein Z is tetrazolyl, Y is oxygen and X$^1$ is a methine group may be obtained, for example, using an analogous procedure to that illustrated in Scheme 2, steps (i)–(vi), but starting from the appropriately substituted 4-nitrophenol, followed by acid hydrolysis. The compounds of the formula XIII wherein Z is tetrazolyl, Y is oxygen and X$^1$ is a nitrogen atom may be obtained using a similar procedure to that illustrated in Scheme 2, steps (ii)–(vi) but starting from the appropriately substituted 5-nitro-2-[2-(trimethylsilyl)ethoxy]pyridine (itself obtained for example from the reaction of the corresponding 2-chloro-5-nitropyridine with 2-(trimethylsilyl)ethanol under basic conditions), followed by acid hydrolysis. An analogous procedure may also be used for those compounds wherein Y is sulphur starting from a suitably protected 5-nitro-2-mercaptopyridine. Compounds of the formula XIII wherein Z is a group of the formula CO.OR$^6$ may be obtained using similar procedures but using a formula V compound in step (v) or a formula VIII compound in step (vi). The compounds of the formula P$^2$.A.B are known or can be obtained by standard procedures of organic chemistry.

Procedure (e) is also suitable for the production of compounds of the formula III (used as starting material in process (b) above) when in the procedure a compound of the formula XV is used in place of a formula XIII compound. The formula XV compounds may be obtained, for example, using an analogous procedure to process (c) but using as starting materials a compound of the formula VI and a compound of the formula XVI wherein P$^4$ is hydrogen or a protecting group which can subsequently be removed preferentially with respect to the group L. The compounds of the formula XVI may be obtained, for example, using analogous procedures to those used for the preparation of compounds of the formula IV.

(f) For those compounds of formula I in which $X^1$ is a nitrogen atom, a compound of the formula XIV wherein $P^3$ is a suitable leaving group (such as halogeno, typically fluoro, chloro or bromo) is reacted with a compound of the formula HY.A.B.

The reaction is generally carried out in the presence of a suitable base, in a suitable solvent and under similar conditions to those described in process (d).

The compounds of the formula XIV wherein Z is tetrazolyl may be obtained, for example, using an analogous procedure to that illustrated in Scheme 2, steps (iii) and (v), but starting from the appropriately substituted 5-amino-2-halogenopyridine and using in step (v) a compound of the formula V in place of the formula VI compound, followed by acid hydrolysis. Compounds of the formula XIV wherein Z is a group of the formula $—CO.OR^6$ may be obtained using a similar procedure but using a formula V compound in step (v). The compounds of the formula HY.A.B are known or may be obtained by standard procedures of organic chemistry.

It will be appreciated that in the aforementioned processes (a)–(f), or in the preparation of the required starting materials for said processes, it may be necessary to protect one or more functional groups present with a suitable protecting group prior to carrying out the subsequent step or steps, whereafter the protecting group is removed, for example as illustrated in Scheme 2 for the preparation of compounds of the formula III. It will also be appreciated that, in a similar manner to obtaining compounds of the formula III by subsequent modification of a functional group present in a compound of the formula III previously prepared (as described above), other compounds of the formula I may be obtained by subsequent modification of a functional group present in a compound of the formula I previously prepared by one of the processes (a)–(f).

Whereafter, those compounds of formula I wherein Z is 1H-tetrazol-5-yl may be obtained by stepwise conversion of a compound of the formula I wherein Z is a group of the formula $—CO,OR^6$ into the corresponding nitrile under standard conditions, followed by reaction of the nitrile with an azide such as an alkali metal azide, preferably in the presence of an ammonium halide, and preferably in the presence of a suitable polar solvent such as N,N-dimethylformamide and at a temperature in the range, for example, 50° to 160° C.

Whereafter, those compounds of the formula I wherein Z is —CO.NH.(1H-tetrazol-5-yl), a group of the formula $—CO.NH.SO_2\overline{R}^7$ or a group of the formula $—CO.OR^6$ in which $R^6$ is other than hydrogen, may be obtained, for example, by reacting a carboxylic acid of the formula I in which Z is carboxy (or a reactive derivative of said acid) with 5-aminotetrazole, a sulphonamide of the formula $NH_2.SO_2R^7$ or a salt thereof (for example, an alkali metal salt), or a hydroxy compound of the formula $HO.R^6$ or with a salt thereof (for example, an alkali metal thereof). Suitable reactive derivatives include, for example the chloride, bromide, azide, anhydride and mixed anhydride with formic or acetic acid of the carboxylic acid of formula I as defined above. When the free acid form is used, the reaction is generally carried out in the presence of a suitable dehydrating agent such as dicyclohexylcarbodiimide or 3-(3-dimethylaminopropyl)-1-ethylcarbodiimide in the presence of a base such as triethylamine or pyridine. When a reactive derivative is used, either the reaction is carried out in the presence of a base such as mentioned above, or, for the preparation of a compound of the formula I wherein Z is a group of the formula $—CO.NH.SO_2R^7$ or a group of the formula $—CO.OR^6$, the sulphonamide or hydroxy compound is used in the form of a salt, such as its alkali metal salt (in particular the lithium, sodium or potassium salt thereof). The reaction is generally performed in the presence of a suitable diluent or solvent such as dioxan, t-butyl methyl ether or tetrahydrofuran and at a temperature in the range, for example, 0°–60° C.

Whereafter, when a salt of a compound of formula I is required, it may be obtained, for example, by reaction with the appropriate base affording a physiologically acceptable cation, or with the appropriate acid affording a physiologically acceptable anion, or by any other conventional salt formation procedure.

Further, when an optically active form of a compound of formula I is required, one of the aforesaid processes may be carried out using an optically active starting material. Alternatively, the racemic form of a compound of formula I in which Z is an acidic group may be resolved, for example by reaction with an optically active form of a suitable organic base, for example, ephedrine, N,N,N-trimethyl -phenylethyl)ammonium (1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula I may be liberated by treatment with acid using a conventional procedure, for example using an aqueous mineral acid such as dilute hydrochloric acid.

Certain of the intermediates defined herein are novel, for example the compounds of the formula II, III and IV, and are provided as a further feature of the invention.

As stated above, the compounds of formula I will have beneficial pharmacological effects in warm-blooded animals (including man) in diseases and medical conditions where amelioration of the vasoconstrictor and fluid retaining properties of the reninangiotensin-aldosterone system is desirable, at least in part by antagonism of one or more of the physiological actions of AII. The compounds of the invention will thus be useful in the treatment of diseases or medical conditions such as hypertension, congestive heart failure and/or hyper-aldosteronism in warm-blooded animals (including man), as well as in other diseases or medical conditions in which the renin-angiotensin-aldosterone system plays a significant causative role.

The antagonism of one or more of the physiological actions of AII and, in particular, the antagonism of the interaction of AII with the receptors which mediate its effects on a target tissue, may be assessed using one or more of the following, routine laboratory procedures.

Test A: This in vitro procedure involves the incubation of the test compound initially at a concentration of 100 micromolar (or less) in a buffered mixture containing fixed concentrations of radiolabelled AII and a cell surface membrane fraction prepared from a suitable angiotensin target tissue. In this test, the source of cell surface membranes is the guinea pig adrenal gland which is well known to response to AII. Interaction of the radiolabelled AII with its receptors (assessed as radiolabel bound to the particulate membrane fraction following removal of unbound radiolabel by a rapid filtration procedure such as is standard in such studies) is antagonized by compounds which also bind to the membrane receptor sites and the degree of antagonism (observed in the test as displacement of membrane-bound radioactivity) is determined readily by comparing the receptor-bound radioactivity in the presence of the test compound at the specified test concentration with a control value determined in the absence of the test compound. Using this procedure compounds showing at least 50% displacement of radiolabelled AII binding at a concentration of $10^{-4}$M are retested at lower concentrations to determine their potency. For determination of the $IC_{50}$ (concentration for 50% displacement of radiolabelled AII binding), concentrations of the test compound are ordinarily chosen to allow testing over at least four orders of magnitude centred about the predicted approximate $IC_{50}$, which latter is subsequently determined from a plot of percentage displacement against concentration of the test compound.

In general, acidic compounds of formula I as defined above show significant inhibition in Test A at a concentration of 50 micromolar or much less.

Test B: This in vitro test involves the measurement of the antagonistic effects of the test compound against AII-induced contractions of isolated rabbit aorta, maintained in a physiological salt solution at 37° C. In order to ensure that the effect of the compound is specific to antagonism of AII, the effect of the test compound on noradrenaline-induced contractions may also be determined in the same preparation.

In general, compounds of formula I as defined above wherein Z is an acidic group show significant inhibition in Test B at a final concentration of 50 micromolar or much less. [Note: Compounds of formula I wherein Z is a group of the formula —CO.OR$^6$ in which R$^6$ is other than hydrogen in general show only weak activity in the in vitro Tests A or B.]

Test C: This in vivo test involves using terminally-anaesthetised or conscious rats in which an arterial catheter has been implanted under anaesthesia for the measurement of changes in blood pressure. The AII antagonistic effects of the test compound following oral or parenteral administration, are assessed against pressor responses induced by AII. To ensure that the effect is specific the effect of the test compound on vasopressin-induced pressor responses may also be determined in the same preparation.

The compounds of formula I generally show specific AII-antagonist properties in Test C at a dose of 50 mg/kg body weight or much less, without any overt toxicological or other untoward pharmacological effect.

Test D: This in vivo test involves the stimulation of endogenous AII biosynthesis in a variety of species including rat, marmoset and dog by introducing a diet of low sodium content and giving appropriate daily doses of a saluretic known as frusemide. The test compound is then administered orally or parenterally to the animal in which an arterial catheter has been implanted under anaesthesia for the measurement of changes in blood pressure.

In general compounds of formula I will show AII-antagonist properties in Test D as demonstrated by a significant reduction in blood pressure at a dose of 50 mg/kg body weight or much less, without any overt toxicological or other untoward pharmacological effect.

By way of illustration of the angiotensin II inhibitory properties of compounds of the formula I, the compound of Example 2 gave the following results in tests A and C described above:

In test A: an $IC_{50}$ of $1.8 \times 10^{-8}$M;

In test C: an $ED_{50}$ of 0.08 mg/kg (i.v. administration).

The compounds of formula I will generally be administered for therapeutic or prophylactic purposes to warm-blooded animals (including man) requiring such treatment in the form of a pharmaceutical composition, as is well known in the pharmaceutical art. According to a further feature of the invention there is provided a pharmaceutical composition comprising a compound of formula I or a salt thereof as defined above, together with a pharmaceutically acceptable diluent or carrier. Such compositions will conveniently be in a form suitable for oral administration (e.g. as a tablet, capsule, solution, suspension or emulsion) or parenteral administration (e.g. as an injectable aqueous or oily solution, or injectable emulsion).

The compounds of formula I may also be advantageously administered for therapeutic or prophylactic purposes together with another pharmacological agent known in the general art to be of value in treating one or more of the diseases or medical conditions referred to hereinabove.

In general a compound of formula I (or a pharmaceutically acceptable salt thereof as appropriate) will generally be administered to man so that, for example, a daily oral dose of up to 50 mg/kg body weight (and preferably of up to 10 mg/kg) or a daily parenteral dose of up to 5 mg/kg body weight (and preferably of up to 1 mg/kg) is received, given in divided doses as necessary, the precise amount of compound (or salt) administered and the route and form of administration depending on size, age and sex of the person being treated and on the particular disease or medical condition being treated according to principles well known in the medical arts.

In addition to their aforesaid use in therapeutic medicine in humans, the compounds of formula I are also useful in the veterinary treatment of similar conditions affecting commercially valuable warm-blooded animals, such as dogs, cats, horses and cattle. In general for such treatment, the compounds of the formula I will generally be administered in an analogous amount and manner to those described above for administration to humans. The compounds of formula I are also of value as pharmacological tools in the development and standardisation of test systems for the evaluation of the effects of AII in laboratory animals such as cats, dogs, rabbits, monkeys, rats and mice, as part of the continuing search for new and improved therapeutic agents.

The invention will now be illustrated by the following nonlimiting Examples in which, unless otherwise stated:

(i) concentrations and evaporations were carried out by rotary evaporation in vacuo;

(ii) operations were carried out at room temperature, that is in the range 18°–26° C.;

(iii) flash column chromatography was performed on Merck Kieselgel 60 (Art. No. 9385) obtained from E Merck, Darmstadt, Germany;

(iv) yields, where given, are intended for the assistance of the reader only and are not necessarily the maximum attainable by diligent process development;

(v) proton NMR spectra were normally determined at 200 MHz in CDCl$_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet; and (vi) all end-products had satisfactory microanalyses.

EXAMPLE 1

Concentrated hydrochloric acid (20 ml) was added to a hot suspension of 2-ethyl-6-(2-hydroxyethoxy)-4-[(2'-(2-triphenylmethyl2H-tetrazol-5-yl)biphenyl-4-yl)methoxy]-1,5-naphthyridine (A) (6.3 g) in ethanol (60 ml). The resulting solution was allowed to cool and left to stand for 1 hour. Volatile material was removed by evaporation and the residue was triturated with ethanol to give 2-ethyl-6-(2-hydroxyethoxy)-4-[(2'-(1H-tetrazol-5-yl)biphenyl-4-yl)methoxy]-1,5-naphthyridine hydrochloride (3.8 g), as a white powder, m.p. 180°–181° C.; NMR (d$_6$-DMSO): 1.4(t,3H), 3.2(q,2H), 3.85(t,2H), 4.5(t,2H), 5.65(s,2H), 7.2(d,2H), 7.5–7.8 (complex m,8H), 8.6(d,1H); $^{13}$C NMR: (benzylic CH$_2$) 71.5; mass spectrum (+ve FAB, DMSO/m-nitrobenzyl alcohol (NBA)): 469 (M+H)$^+$; microanalysis, found: C,61.2; H,4.9; N,16.2; H$_2$O, 0.6%; C$_{26}$H$_{24}$N$_6$O$_3$.HCl.0.25H$_2$O requires: C,61.3; H,5.0; N,16.5; H$_2$O, 0.9%.

The starting material A was obtained as follows:-

(i) 2-(2-Hydroxyethoxy)-5-nitropyridine (obtained as described in *Annalen der Chemie.*, 1936, 521, 286) (114 g) was added portionwise to an ice-cooled, stirred suspension of sodium hydride (60% dispersion in mineral oil; 24.8 g) in N,N-dimethylformamide (DMF) (600 ml), at such a rate that the temperature did not exceed 10° C. The solution was stirred at 0° C. for 10 minutes, and then tert-butylchlorodiphenylsilane (171 g) was added dropwise at such a rate that the temperature did not exceed 10° C. The solution was stirred for 72 hours and then added to water (2 l). The mixture was extracted with ethyl acetate (2 ×1 l), and the extracts were washed with water (1 l) and saturated sodium chloride solution (500 ml), and then dried (MgSO$_4$). Volatile material was removed by evaporation, and the residue was purified by flash chromatography, eluting with hexane to give 2-[2-(t-butyldiphenylsilyl)oxyethoxy]-5-nitropyridine (B) (106 g) as an oil which solidified on standing, m.p. 63°–64° C. (from hexane); NMR (d$_6$-DMSO): 1.0(s,9H), 4.0(t,2H), 4.55(t,2H), 7.0(d,1H), 7.3–7.5(m,6H), 7.55–7.75(m,4H), 8.45(dd,1H), 9.0(d,1H).

(ii) Compound B (106 g) was dissolved in methanol (1.35 l) and hydrogenated at atmospheric pressure over 10% palladium on charcoal catalyst (10.6 g). When hydrogen uptake was complete, the catalyst was removed by filtration through diatomaceous earth. Volatile material was then removed from the filtrate by evaporation to give 5-amino-2-[2-(t-butyldiphenylsilyl)oxyethoxy]pyridine (C) (99.4 g), as an oil which was used without further purification; NMR (d$_6$-DMSO): 0.95(s,9H), 3.9(t,2H), 4.25(t,2H), 4.7(brs,2H), 6.5(d,1H), 7.0(dd,1H), 7.35–7.75 (complex m,7H), 7.6–7.75(m,4H).

(iii) A solution of compound C (89.5 g), methyl propionylacetate (32.8 g) and p-toluenesulphonic acid (1.0 g) in cyclohexane (900 ml) was heated under reflux with azeotropic removal of water for 20 hours. Volatile material was then removed from the reaction mixture by evaporation and the residue was dissolved in ethyl acetate (1 l). The solution was washed with saturated sodium hydrogen carbonate solution (500 ml), water (500 ml), saturated sodium chloride solution (500 ml), and then dried (MgSO$_4$). The solvent was removed by evaporation and the residue dissolved in a eutectic mixture of 26.5% v/v diphenyl and 73.5% v/v diphenyl oxide (750 ml). The solution was heated to 260° C. and the temperature maintained for 30 minutes. The solution was cooled and diluted with hexane (1 l) to give 6-[2-(t-butyldiphenylsilyl)oxyethoxy]-2-ethyl-1,5-naphthyridin-4(1H)-one (D) (55.4 g), as a white solid, m.p. 209°–210° C.; NMR (d$_6$-DMSO): 1.1(s,9H), 1.35(t,3H), 2.8(q,2H), 4.15(t,2H), 4.65(t,2H), 6.3(br s,1H), 7.25(d,1H), 7.5–7.6(m,7H), 7.65–7.8(m,4H), 8.1(d,1H).

(iv) Compound D (27.7 g) was added to a stirred suspension of sodium hydride (60% dispersion in mineral oil; 2.6 g) in DMF (300 ml). The mixture was allowed to stir until hydrogen evolution ceased, and then 5-[(2-(4'-bromoethylbiphenylyl)]-2-triphenylmethyl-2H-tetrazole (32.7 g) (obtained as described in European patent application, publication number 291969) was added. Stirring was continued for 20 hours and then the mixture was added to water (1 l). The insoluble solid was collected by filtration and the residue purified by flash chromatography, eluting initially with ethyl acetate and then with methanol/ethyl acetate (1:9 v/v), to give 6-[2-(t-butyldiphenylsilyl)oxyethoxy]-2-ethyl-4-[(2'-(2-triphenylmethyl-2H-tetrazol-5-yl) biphenyl-4-yl)methoxy]-1,5-naphthyridine (E), (32.1 g), as a foam, NMR (d$_6$-DMSO): 0.9(s,9H), 1.3(t,3H), 2.85(q,2H), 4.0–4.1(m,2H), 4.5–4.6(m,2H), 5.35(s,2H), 6.8–6.9(m,6H), 7.1(d,2H), 7.2(d,2H), 7.25–7.75 (complex m,18H), 7.55–7.65(m,6H), 7.85(dd,1H), 8.2(dd,1H).

(v) A 1M solution of tetrabutylammonium fluoride in tetrahydrofuran (THF) (67.8 ml) was added to a solution of compound E (32.1 g) in dry THF (400 ml), and the solution was left to stand for 1 hour. The solution was then diluted with ethyl acetate (400 ml), washed with water (400 ml) and dried (MgSO$_4$). Volatile material was removed by evaporation, and the residue triturated with ether to give 2-ethyl-6-(2-hydroxyethoxy)-4-[(2'-(2-triphenylmethyl-2H-tetrazol-5-yl)biphenyl-4-yl)methoxy]-1,5-naphthyridine (A) (21.6 g), as a white solid, m.p. 170°–173° C.; NMR (d$_6$-DMSO): 1.3(t,3H), 2.85(q,2H), 3.75(q,2H), 4.45(t,2H), 4.85(t,1H), 5.35(s,2H), 6.8–6.9(m,7H), 7.1–7.7 (complex m,17H), 7.8(dd,1H), 8.15(d,1H).

EXAMPLE 2

Concentrated hydrochloric acid (0.1 ml) was added to a solution of 2-ethyl-6-(2-(ethylaminocarbonyloxy)ethoxy)-4-[2'-(2-triphenylmethyl-2H-tetrazol-5-yl)biphenyl-4-yl)methoxy] 1,5-naphthyridine (A) (300 mg) in methanol (5 ml). After 10 minutes volatile material was removed by evaporation and the residue dissolved in 1-propanol (5 ml) and diluted with ether (20 ml) to precipitate 2-ethyl-6-(2-ethylaminocarbonyloxy)ethoxy)-4-[(2'-(1H-tetrazol-5-yl)biphenyl-4-yl)methoxy]-1,5-naphthyridine hydrochloride (180 mg), as a white solid, m.p. 112°–122° C.; NMR (d$_6$-DMSO) 1.0(t,3H), 1.4(t,3H), 2.9–3.2(m,4H), 4.35(m,2H), 4.65(m,2H), 5.65(s,2H), 7.2(d,2H), 7.5–7.8(m,8H), 8.65(d,1H); mass spectrum (+ve FAB, DMSO/NBA): 540 (M+H)$^+$.

The starting material (A) was obtained as follows:

(i) Sodium hydride (56 mg) was added to a solution of 2-ethyl-6-(2-hydroxyethoxy)-4-[(2'-(2-triphenylmethyl-2H-tetrazol5-yl)biphenyl-4-yl)methoxy]-1,5-naphthyridine (1.0 g) in THF (44 ml) under an argon atmosphere. The mixture was stirred until evolution of hydrogen had ceased and then cooled to 15° C. Ethyl isocyanate (0.12 ml) was added dropwise and the mixture was stirred for 16 hours. Water (10 ml) was added, the mixture extracted with ether (2×20 ml) and the combined extracts dried (MgSO$_4$) and evaporated. The residue was purified by flash chromatography eluting with ethyl acetate/hexane (1:1 v/v) to give 2-ethyl-6-(2-ethylaminocarbonyloxy)ethoxy)-4-[(2'-(2-triphenylmethyl-2H-tetrazol-5-yl)biphenyl-4-yl)methoxy]-1,5-naphthyridine (A) (365 mg), as a white powder, m.p. 79°–80° C.; NMR (d$_6$-DMSO): 0.9(t,3H), 1.25(t,3H), 2.8(q,2H), 3.0(m,2H), 4.30(m,2H), 4.6(m,2H), 5.35(s,2H), 6.85(m,5H), 7.15–7.85(m,20H), 8.15(d,1H).

EXAMPLE 3

Concentrated hydrochloric acid (1.6 ml) was added to a suspension of 2-ethyl-6-(ethoxycarbonylmethoxy)-4-[(2'-(2-triphenylmethyl-2H-tetrazol-5-yl)biphenyl-4-yl)methoxy]-1,5-naphthyridine (A) (0.61 g) in ethanol (9.7 ml) and the resulting solution was stirred for three hours. The precipitated solid was collected by filtration and recrystallised from methanol to give 2-ethyl-6-(ethoxycarbonylmethoxy)-4-[2'-(1H-tetrazol-5-yl)biphenyl-4-yl)methoxy]-1,5-naphthyridine hydrochloride (0.139 g), as a white powder, m.p. 191°–193° C.; NMR (d$_6$-DMSO): 1.0(t,3H), 1.4(t,3H), 3.1(q,2H), 4.0(q,2H), 5.0(s,2H), 5.6(s,2H), 7.2(d,2,H), 7.6(m,8H), 8.7(d,1H); mass spectrum (+ve FAB, DMSO/NBA): 511 (M+H)$^+$.

The starting material A was obtained as follows:

(i) Potassium t-butoxide (25.8 g) was added portionwise over 20 minutes to a solution of 2-(trimethylsilyl)ethanol (20.8 g) and 2-chloro-5-nitropyridine (27.8 g) in DMF (170 ml). The mixture was stirred for 18 hours and then poured into ice-water (900 ml). The mixture was extracted with ethyl acetate (3×300 ml) and the extracts were washed with water (200 ml), followed by saturated sodium chloride solution (200 ml) and dried (MgSO$_4$). Volatile material was removed by evaporation to give 5-nitro-2-[2-(trimethylsilyl)ethoxy]pyridine (B) (34.9 g) as an oil; NMR: 0.05(s,9H), 1.1–1.2(m,2H), 4.45–4.55(m,2H), 6.75(d,1H), 8.3(dd,1H), 9.05(d,1H).

(ii) Compound B (36.8 g) was dissolved in ethanol (270 ml) and catalytically hydrogenated at atmospheric pressure over platinum oxide (300 mg). The catalyst was removed by filtration through diatomaceous earth. The solvent was removed by evaporation and the residue triturated with hexane to give 5-amino-2-[2-(trimethylsilyl)ethoxy]pyridine (C) (20.0 g), as dark crystals, m.p. 59°–61° C.; NMR: 0.0(s,9H), 0.95–1.05(m,2H), 3.1–3.3(br s, 2H), 4.2–4.3(m,2H), 6.5(d,1H), 6.95(dd,1H), 7.6(d,1H).

(iii) A solution of compound C (10 g), methyl propionylacetate (11.5 g) and p-toluenesulphonic acid (0.1 g) in benzene (40 ml) was heated under reflux with azeotropic removal of water for 20 hours. Volatile material was removed by evaporation and the residue added to a refluxing eutectic mixture of 26.5% v/v diphenyl and 73.5% v/v diphenyl oxide (30 ml). The solution was heated under reflux for 1 hour, cooled and diluted with hexane (100 ml). The precipitated solid was filtered off and triturated with hot methanol (100 ml) to give 2-ethyl-6-[2-(trimethylsilyl)ethoxy]-1,5-naphthyridin-4-(1H)-one (D) (in 62% yield) as a white solid, m.p. 193° C.; NMR: −0.1(s,9H), 0.85(t,2H), 1.3(t,3H), 2.8(q,2H), 4.1(t,2H), 6.55(s,1H), 6.9(d,1H), 8.2(d,1H).

(iv) Compound D (7.1 g) was added to a stirred suspension of sodium hydride (60% dispersion in mineral oil; 1.08 g) in DMF (50 ml). The mixture was stirred at 50° C. until evolution of hydrogen had ceased and then a slurry of 5-[(2-(4'-bromomethylbiphenylyl)]-2-triphenylmethyl-2H-tetrazole (13.7 g) in DMF (20 ml) was added. Stirring was continued for 20 hours and then the mixture was added to water (400 ml). The precipitated solid was collected by filtration and purified by flash chromatography, eluting with ethanol/ethyl acetate (2:98 v/v), to give 2-ethyl-6-[2-(trimethylsilyl)ethoxy]-4-[2'-(2-triphenylmethyl-2H-tetrazol-5-yl)biphenyl-4-yl)methoxy]-1,5-naphthyridine (E) (in 75% yield), as a white solid, m.p. 113°–115° C.; NMR: 0.05(s,9H), 1.1–1.2(m,2H), 1.35(t,3H), 2.9(q,2H), 4.55–4.65(m,2H), 5.2(s,2H), 6.8–7.5 (complex m,24H), 7.85–7.95(m,1H), 8.1(d,1H).

(v) A 1M solution of tetrabutylammonium fluoride in THF (14 ml) was added to a solution of compound E (1.1 g) in THF (10 ml) and the mixture was stirred for 2 hours. The solution was then warmed to 40° C. for 10 minutes. Volatile material was removed by evaporation and the residual oil was dissolved in ethyl acetate (75 ml) and washed with water (75 ml and 30 ml). The precipitated solid was collected by filtration to give 2-ethyl-6-hydroxy-4-[(2'-triphenylmethyl-2H-tetrazol-5-yl)biphenyl-4-yl)-methoxy]-1,5-naphthyridine (F) (0.83 g) as a white solid, m.p. 148°–149° C.; NMR (d$_6$-DMSO): 1.2(t,3H), 2.7(q,2H), 5.3(s,2H), 6.65–7.9(m,26H), 11.1(s,1H).

(vi) Ethyl chloroacetate (0.16 ml) was added to a mixture of compound F (1.0 g), potassium carbonate (0.21 g) and DMF (20 ml). The resulting mixture was stirred for 16 hours and then poured into water (200 ml). The precipitated solid was collected by filtration, washed with water (20 ml), and then purified by flash chromatogrphy, eluting with ethyl acetate/hexane (1:1 v/v). There was thus obtained 2-ethyl-6-(ethoxycarbonylmethoxy)-4-[(2'-(2-triphenylmethyl-2H-tetrazol-5-yl)biphenyl-4-yl)methoxy]-1,5-naphthyridine (A) (0.65 g), m.p. 131.5°–133° C.; NMR: 1.0(t,3H), 1.3(t,3H), 2.8(q,2H), 4.0(q,2H), 5.0(s,2H), 5.3(s,2H), 6.9(m,6H), 7.1(d,2H), 7.3(m,12H), 7.5(d,2H), 7.6(d,2H), 7.8(d,1H), 8.2(d,1H).

EXAMPLE 4

Using an analogous procedure to that described in Example 1, but starting from 2-ethyl-6-(2-methoxyethoxy)-4-[(2'-(2-triphenylmethyl-2H-tetrazol-5-yl)biphenyl-4-yl)methoxy]-1,5-naphthyridine (A), there was obtained in 75% yield 2-ethyl-6-(2-methoxyethoxy)-4-[(2'-(1H-tetrazol-5-yl)biphenyl-4-yl)methoxy]-1,5-naphthridine hydrochloride, m.p. 142°–144° C.; NMR (d$_6$-DMSO): 1.4(t, 3H), 3.15(q, 2H), 3.3(s, 3H), 3.7–3.8(m, 2H), 4.5–4.6(m, 2H), 5.65(s, 2H), 7.2(d, 2H), 7.5–7.8(complex m, 8H), 8.6(d, 1H); mass spectrum (+ve FAB, DMSO/NBA): 483(M+H)$^+$; microanalysis, found: C, 61.4; H, 5.2; N, 15.9; Cl, 6.5; H$_2$O, 0.5%; C$_{27}$H$_{26}$N$_6$O$_3$.HCl.0.15H$_2$O.0.2(CH$_3$CO$_2$C$_2$H$_5$) requires: C, 61.9; H, 5.4; N, 15.6; Cl, 6.6; H$_2$O 0.5%.

The starting material (A) was obtained as follows:

Sodium hydride (60% dispersion in mineral oil, 62 mg) was added in a solution of 2-ethyl-6-(2-hydroxyethoxy)-4-[(2'-(2-triphenylmethyl-2H-tetrazol-5-yl)biphenyl-4-yl)methoxy]-1,5-naphthyridine (1.0 g) in THF (10 ml). The mixture was stirred until evolution of hydrogen had ceased and then methyl iodide (0.09 ml) was added. The solution was left to stand for.72 hours and then water (30 ml) was added. The mixture was extracted with ether (2×20 ml) and the combined extracts were dried (MgSO₄). Volatile material was removed by evaporation and the residue was triturated with hexane to give 2-ethyl-6-(2-methoxyethoxy)-4-[(2'-(2-triphenylmethyl-2H-tetrazol-5-yl)biphenyl-4-yl)methoxy]-1,5-naphthyridine (A) (0.86 g), as a foam; NMR (d₆-DMSO): 1.3(t, 3H), 2.8(q, 2H), 3.25(s, 3H), 3.6–3.7(m, 2H), 4.45–4.55(m, 2H), 5.4(s, 2H), 6.8–6.9(m, 6H), 7.1–7.7(complex m, 18H), 7.8(dd, 1H), 8.15(d, 1H).

EXAMPLE 5

Using an analogous procedure to that described in Example 1, but starting from 2-ethyl-6-[2-(4-morpholinocarbonyloxy)ethoxy]-4-[(2'-(2-triphenylmethyl-2H-tetrazol-5-yl)biphenyl-4-yl)methoxy]-1,5-naphthyridine (A), there was obtained in 93% yield 2-ethyl-6-[2-(4-morpholinocarbonyloxy)ethoxy]-4-[(2'-(1H-tetrazol-5-yl)biphenyl-4-yl)methoxy]-1,5-naphthyridine hydrochloride, m.p. 161°–164° C.; NMR (d₆-DMSO+d₄-acetic acid): 1.45(t, 3H), 3.1(q, 2H), 3.25–3.6(complex m, 8H), 4.4–4.55(m, 2H), 4.65–4.8(m, 2H), 5.2(s, 2H), 7.2–7.3(m, 3H), 7.5–7.8(m, 7H), 8.5(d, 1H); mass spectrum (+ve FAB, DMSO/NBA): 582 (M+H)⁺; microanalysis, found: C, 59.9; H, 5.3; N, 15.7; Cl, 5.7%; C₃₁H₃₁N₂O₅.HCl requires: C, 60.2; H, 5.2; N, 15.9; Cl, 54%;

The starting material (A) was obtained as follows:

Sodium hydride (60% dispersion in mineral oil, 62 mg) was added to a solution of 2-ethyl-6-(2-hydroxyethoxy)-4-[(2'-(2-triphenylmethyl-2H-tetrazol-5-yl)biphenyl-4-yl)methoxy]-1,5-naphthyridine (1.0 g) in THF (10 ml). The mixture was stirred until evolution of hydrogen had ceased and then 1-(4-morpholinocarbonyl)imidazole (285 mg) in THF (10 ml) was added. The solution was heated under reflux for 3 hours and then cooled. Ether (50 ml) was added and the solution was washed with water (2×30 ml) and dried (MgSO₄). Volatile material was removed by evaporation an the residue was recrystallised from a mixture of ether and hexane to give 2-ethyl-6-[2-(4-morpholinocarbonyloxy)ethoxy]-4-[(2'-(2-triphenylmethyl-2H-tetrazol-5-yl)biphenyl-4-yl)methoxy]-1,5-naphthyridine (A) (0.82 g), m.p. 76°–79° C.; NMR (d₆-DMSO): 1.3(t, 3H), 2.85(q, 2H), 3.2–3.3(m, 4H), 3.3–3.5(m, 4H), 4.3–4.4(m, 2H), 4.6–4.7(m, 2H), 5.35(s, 2H), 6.8–6.9(m, 6H), 7.1–7.7(complex m, 18H), 7.8(dd, 1H), 8.15(d, 1H),

EXAMPLE 6

Using an analogous procedure to that described in Example 1, but starting from 2-ethyl-6-[2-(1-(4-methyl)-piperazinocarbonyloxy) ethoxy]-4-[(2'-(2-triphenylmethyl-2H-tetrazol-5-yl)biphenyl-4-yl) methoxy]-1,5-naphthyridine (A), there was obtained in 60% yield 2-ethyl-6-[2-(1-(4-methyl)piperazinocarbonyloxy)ethoxy]-4-[(2'-(1H-tetrazol-5-yl)biphenyl-4-yl)methoxy]-1,5-naphthyridine dihydrochloride, m.p. 136°–139° C.; NMR (d₆-DMSO+d₄-acetic acid): 1.45(t, 3H), 2.8(s, 3H), 2.9–3.4(complex m, 10H), 4.45–4.55(m, 2H), 4.65–4.75(m, 2H), 5.7(s, 2H), 7.25(d, 2H), 7.5–7.8(m, 8H), 8.6(d, 1H); mass spectrum (+ve FAB, DMSO/NBA): 595 (M+H)⁺.

The starting material (A) was obtained as a foam in 55% yield using an analogous procedure to that described in Example 5 but employing 1-[1-(4-methyl)-piperazinocarbonyl]imidazole; NMR (d₆-DMSO): 1.3(t, 3H), 1.95–2.2(m, 7H), 2.85(q, 2H), 3.2–3.3(m, 4H), 4.3–4.4(m, 2H), 4.6–4.7(m, 2H), 5.4(s, 2H), 6.8–6.95(m, 6H), 7.1–7.75(complex m, 18H), 7.85(dd, 1H), 8.15(d, 1H).

EXAMPLE 7

Using an analogous procedure to that described in Example 1, but starting from 2-ethyl-6-[2-(4-morpholino)ethoxy]-4-[-(2'-(2-triphenylmethyl-2H-tetrazol-5-yl)biphenyl-4-yl)methoxy]-1,5-naphthyridine (A), there was obtained in 68% yield 2-ethyl-6-[2-(4-morpholino)ethoxy]-4-[(2'-(1H-tetrazol-5-yl)biphenyl-4-yl)methoxy]-1,5-naphthyridine dihydrochloride, m.p. 186°–188° C.; NMR (d₆-DMSO+d₄-acetic acid): 1.45(t, 3H), 3.15(q, 2H), 3.35–3.6(m, 4H), 3.7–3.8(m, 2H), 3.85–4.0(m, 4H), 4.85–4.95(m, 2H), 5.65(s, 2H), 7.25(d, 2H), 7.5–7.8(complex m, 8H), 8.55(d, 1H); mass spectrum (+ve FAB, DMSO/NBA): 538 (M+H)⁺.

The starting material (A) was obtained as follows:

(i) DMSO (2.0 ml) and phosphorus pentoxide (4.0 g) were added to a solution of 2-ethyl-6-(2-hydroxyethoxy)-4-[(2'-(2-triphenylmethyl-2H-tetrazol-5-yl)biphenyl-4-yl)methoxy]-1,5-naphthyridine (1.0 g) in dichloromethane (20 ml) at 0° C. The mixture was stirred at ambient temperature for 1 hour and then cooled again to 0° C. Triethylamine (0.69 ml) was added and stirring was continued for 30 minutes. 1M citric acid solution (20 ml) was added and the organic phase was separated and dried (MgSO₄). The solvent was removed by evaporation and the residue was purified by flash chromatography, eluting with ethyl acetate/hexane (1:1 v/v), to give 2-ethyl-6-(formylmethoxy)-4-[(2'-(2-triphenylmethyl-2H-tetrazol-5-yl)biphenyl-4-yl)methoxy]-1,5-naphthyridine (B) (0.46 g), m.p. 168°–169° C. (after trituration with ether; NMR (d₆-DMSO): 1.25(t, 3H), 2.9(q, 2H), 5.0(s, 2H), 5.35(s, 2H), 6.8–6.95(m, 6H), 7.1–7.85(m, 19H), 8.25(d, 1H), 9.7(s, 1H).

(ii) A saturated solution of hydrogen chloride in ethanol (0.1 ml) was added to a solution of compound B (600 mg) and morpholine (450 mg) in methanol (10 ml) containing 3A molecular sieves (1 g). Sodium cyanoborohydride (53 mg) was added and the mixture was stirred for 20 hours. Volatile material was removed by evaporation and the residue purified by flash chromatography, eluting with methanol/ethyl acetate (1:9 v/v). to give 2-ethyl-6-[2-(4-morpholino)ethoxy]-4-[(2'-(2-triphenylmethyl-2H-tetrazol-5-yl)biphenyl-4-yl)methoxy]-1,5-naphthyridine (A) (152 mg), m.p. 135°–137° C. (after trituration with hexane); NMR (d₆-DMSO): 1.3(t, 3H), 2.3–2.45(m, 4H), 2.6–2.8(m, 2H), 2.85(q, 2H), 3.4–3.55(m, 4H), 4.45–4.6(m, 2H), 5.4(s, 2H), 6.8–6.9(m, 6H), 7.1–7.7(complex m, 18H), 7.8(dd, 1H), 8.15(d, 1H).

EXAMPLES 8–13

Using an analogous procedure to that described in Example 3, but starting from an appropriate compound of formula III (L=triphenylmethyl) the following compounds of formula I were obtained in yields of 34–90%.

Example 8

6-(Aminocarbonylmethoxy)-2-ethyl-4-[(2'-(1H-tetrazol-5-yl)biphenyl-4-yl)methoxy]-1,5-naphthyridine hydrochloride, m.p. 172°–176° C.; NMR (d₆-DMSO+d₄-acetic acid): 1.4(t, 3H), 3.1(q, 2H), 5.0(s, 2H), 5.6(s, 2H), 7.3(d, 2H), 7.4–7.7(m, 6H), 7.75(t, 2H), 8.5(d, 1H); mass spectrum (+ve FAB, DMSO/NBA): 482 (M+H)⁺; microanalysis, found: C, 58.2; H, 5.0; N, 18.2; Cl, 6.3; H₂O, 3.7%; C₂₆H₂₃N₇O₃.HCl requires: C, 58.1; H, 4.8; N, 18.2; Cl, 6.6; H₂O, 3.3%.

Example 9

6-[N,N-Diethylaminocarbonyl)methoxy]-2-ethyl-4-[(2'-(1H-tetrazol-5-yl)biphenyl-4-yl)methoxy]-1,5-naphthyridine hydrochloride, m.p. 202°–204° C.; NMR (d$_6$-DMSO+d$_4$-acetic acid): 0.9(t, 6H), 1.4(t, 3H), 3.0–3.2(m, 4H), 5.1(s, 2H), 5.6(s, 2H), 7.2(d, 2H), 7.4–7.8(m, 8H), 8.6(d, 1H); mass spectrum (+ve FAB, DMSO/NBA): 538 (M+H)$^+$; microanalysis, found: C, 61.1; H, 5.6; N, 16.5; Cl, 5.8; H$_2$O 3.0%; C$_{30}$H$_{31}$N$_7$O$_3$.HCl.H$_2$O requires: C, 60.9; H, 5.8; N, 16.6; Cl, 6.0; H$_2$O, 3.0%.

Example 10

6-[1-(Ethoxycarbonyl)ethoxy]-2-ethyl-4-[(2'-(1H-tetrazol-5-yl)biphenyl-4-yl)methoxy]-1,5-naphthyridine hydrochloride, m.p. 194°–196° C.; NMR (d$_6$-DMSO+d$_4$-acetic acid): 1.0(t, 3H), 1.4(t, 3H), 1.6(d, 3H), 3.1(q, 2H), 4.0(q, 2H), 5.4(q, 1H), 5.6(s, 2H), 7.2(d, 2H), 7.4–7.8(m, 8H), 8.5(d, 1H); mass spectrum (+ve FAB, DMSO/NBA): 525 (M+H)$^+$; microanalysis, found: C, 62.0; H, 5.2; N, 15.0; Cl, 6.1% C$_{29}$H$_{28}$N$_6$O$_4$ requires: C, 62.1; H, 5.2; N, 15.0; Cl, 6.3%.

Example 11

6-Benzyloxy-2-ethyl-4-[(2'-(1H-tetrazol-5-yl)biphenyl-4-yl)methoxy]-1,5-naphthyridine hydrochloride, m.p. 144°–147° C; NMR (d$_6$-DMSO+d$_4$-acetic acid): 1.4(t, 3H), 3.1(q, 2H), 5.5(s, 2H), 5.7(s, 2H), 7.1–7.4(m, 6H), 7.45–7.75(m, 9H), 8.5(d, 1H); mass spectrum (−ve FAB, CH$_3$OH/NBA): 513 (M-H)$^−$; microanalysis, found: C, 66.0; H, 5.1; N, 14.1; Cl, 5.9; H$_2$O 3.2%; C$_{31}$H$_{26}$N$_6$O$_2$.HCl.H$_2$O requires: C, 65.4; H, 5.1; N, 14.8; Cl, 6.2; H$_2$O, 3.2%.

Example 12

2-Ethyl-4-[(2'-(1H-tetrazol-5-yl)biphenyl-4-yl)methoxy]-6-[(thiazol-4-yl)methoxy]-1,5-naphthyridine hydrochloride, m.p. 153°–158° C.; NMR (d$_6$-DMSO+d$_4$-acetic acid): 1.4(t, 3H), 3.2(q, 2H), 5.55(s, 2H), 5.65(s, 2H), 7.2(d, 2H), 7.5–7.9(m, 9H), 8.6(d, 1H), 9.1(s, 1H); mass spectrum (+ve FAB, DMSO/NBA): 522 (M+H)$^+$.

Example 13

2-Ethyl-4-[(2'-(1H-tetrazol-5-yl)biphenyl-4-yl)methoxy]-6-[(1,2,5-thiadiazolyl)methoxy]-1,5-naphthyridine hydrochloride, m.p. 185°–189° C.; NMR (d$_6$-DMSO+d$_4$-acetic acid): 1.4(t, 3H), 3.1(q, 2H), 5.6(s, 2H), 5.8(s, 2H), 7.2(d, 2H), 7.4–7.8(m, 8H), 8.6(d, 1H), 8.85(s, 1H); mass spectrum (+ve FAB, CHCl$_3$/NBA): 523 (M+H)$^+$.

The necessary starting materials of formula III were obtained in yields of 36–54% using an analogous procedure to that described in Example 3, part (vi), but substituting the appropriate alkylating agent for ethyl chloroacetate. The compounds of formula III had the following properties:

6-(Aminocarbonylmethoxy)-2-ethyl-4-[(2'-(2-triphenylmethyl-2H-tetrazol-5-yl)biphenyl-4-yl)methoxy]-1,5-naphthyridine, m.p. 180°–183° C.; NMR (d$_6$-DMSO): 1.3(t, 3H), 2.8(q, 2H), 4.8(s, 2H), 5.3(s, 2H), 6.8–6.9(m, 6H), 7.2(t, 2H), 7.25–7.65(m, 16H), 7.8(dd, 1H), 8.2(d, 1H);

6-[(N,N-Diethylaminocarbonyl)methoxy]-2-ethyl-4-[(2'-(2-triphenylmethyl-2H-tetrazol-5-yl)biphenyl-4-yl)methoxy]-1,5-naphthyridine, m.p. 189°–191° C.; NMR (d$_6$-DMSO): 0.9(t, 6H), 1.3(t, 3H), 2.8(q, 2H), 3.1(q, 4H), 5.0(s, 2H), 5.3(s, 2H), 6.8–6.9(m, 6H), 7.15(d, 4H), 7.2–7.5(m, 15H), 8.15(d, 1H);

6-[1-(Ethoxycarbonyl)ethoxy]-2-ethyl-4-[(2'-(2-triphenylmethyl-2H-tetrazol-5-yl)biphenyl-4-yl)methoxy]-1,5-naphthyridine, m.p. 143°–145° C.; NMR (d$_6$-DMSO): 0.9(t, 3H), 1.3(t, 3H), 1.5(d, 3H), 2.8(q, 2H), 4.0(q, 2H), 5.3–5.4(m, 3H), 6.8–6.9(m, 6H), 7.2(t, 2H), 7.3–7.7(m, 16H), 7.8(d, 1H), 8.2(d, 1H);

6-Benzyloxy-2-ethyl-4-[(2'-(2-triphenylmethyl-2H-tetrazol-5-yl)biphenyl-4-yl)methoxy]-1,5-naphthyridine, m.p. 120°–124° C.; NMR (d$_6$-DMSO): 1.2(t, 3H), 2.8(q, 2H), 5.35(s, 2H), 5.45(s, 2H), 6.8–6.9(m, 6H), 7.2–7.6(m, 23H), 7.8(dd, 1H), 8.2(d, 1H);

2-Ethyl-4-[(2'-(2-triphenylmethyl-2H-tetrazol-5-yl)biphenyl-4-yl)methoxy]-6-[(thiazol-4-yl)methoxy]-1,5-naphthyridine, m.p. 160°–163° C.; NMR (d$_6$-DMSO): 1.3(t, 3H), 2.8(q, 2H), 5.6(s, 2H), 5.8(s, 2H), 6.8–6.9(m, 6H), 7.0–7.4(m, 13H), 7.5–7.7(m, 7H), 8.2(d, 1H), 9.1(d, 1H);

2-Ethyl-4-[(2'-(2-tri[phenylmethyl-2H-tetrazol-5-yl)biphenyl-4-yl)methoxy]-6-[(1,2,5-thiadiazolyl)methoxy]-1,5-naphthyridine, m.p. 111°–115° C.; NMR (d$_6$-DMSO): 1.3(t, 3H), 2.8(q, 2H), 5.4(s, 2H), 5.7(s, 2H), 6.8–6.9(m, 6H), 7.1-(d, 2H), 7.2–7.7(m, 16H), 7.8(dd, 1H), 8.2(d, 1H), 9.0(s, 1H).

EXAMPLE 14

Concentrated hydrochloric acid (2.7 ml) was added to a solution of 2-ethyl-6-(ethoxycarbonylmethoxy)-4-[(2'-(2-triphenylmethyl-2H-tetrazol-5-yl)biphenyl-4-yl)methoxy]-1,5-naphthyridine (1.0 g) in ethanol (16 ml). The solution was heated at 50° C. for 2 hours and then cooled. 4M Sodium hydroxide solution (10 ml) was added and the solution was heated at 50° C. for 30 minutes and then diluted with water (50 ml). The solution was washed with ether (25 ml) and the aqueous phase was concentrated by evaporation. Water (10 ml) was added to the residue and the suspension was stirred for 1 hour. The insoluble solid was collected by filtration and dissolved in ethanol (7 ml). Concentrated hydrochloric acid was added and the resultant precipitate was collected by filtration to give 6-(carboxymethoxy)-2-ethyl-4-[(2'-(1H-tetrazol-5-yl)biphenyl-4-yl)methoxy]-1,5-naphthyridine hydrochloride, m.p. 223°–225° C.; NMR (d$_6$-DMSO): 1.4(t, 3H), 3.1(q, 2H), 5.0(s, 2H), 5.6(s, 2H), 7.2(d, 2H), 7.4–7.8(m, 8H), 8.7(d, 1H); mass spectrum (+ve FAB, DMSO/NBA): 527 (M+H)$^+$.

EXAMPLE 15

Using an analogous procedure to that described in Example 1, but starting from 2-ethyl-6-(2-hydroxy-2-methyl-1-propoxy)-4-[(2'-(2-triphenylmethyl-2H-tetrazol-5-yl)biphenyl-4-yl)methoxy]-1,5-naphthyridine (A) there was obtained in 58% yield 2-ethyl-6-(2-hydroxy-2-methyl-1-propoxy)-4-[(2'-(1H-tetrazol-5-yl)biphenyl-4-yl) methoxy]-1,5-naphthyridine hydrochloride, m.p. 120°–128° C.; NMR (d$_6$-DMSO +d$_4$-acetic acid): 1.2(s, 6H), 1.4(t, 3H), 3.1(q, 2H), 4.2(s, 2H), 5.7(s, 2H), 7.2(d, 2H), 7.4–7.8(m, 8H), 8.5(d, 1H); mass spectrum (+ve FAB, DMSO/CHCl$_3$/NBA): 497(M+H)$^+$.

The starting material (A) was obtained as follows:

A 3M solution of methyl magnesium iodide in ether (0.96 ml) was added to a solution of 2-ethyl-6-(ethoxycarbonylmethoxy)-4-[(2'-(2-triphenylmethyl-2H-tetrazol-5-yl)biphenyl-4-yl)methoxy]-1,5-naphthyridine (0.95 g) in THF (5 ml) at −20° C. The solution was allowed to warm to ambient temperature and left to stand for 20 hours. Saturated ammonium chloride solution (20 ml) was added and the mixture was extracted with ether (3×10 ml). The extracts were washed with water (2×10 ml) and dried (MgSO$_4$). The solvent was removed by evaporation and the residue was triturated with ether to give 2-ethyl-6-(2-hydroxy-2-methyl-1-propoxy-4-[(2'-(2-triphenylmethyl-2H-tetrazol-5-yl)biphenyl-4-yl)methoxy]-1,5-naphthyridine (A) (353 mg), m.p. 169°–172° C.; NMR (d$_6$-DMSO): 1.1(s, 6H), 1.3(t, 3H), 2.8(q, 2H), 4.2(s, 2H), 5.4(s, 2H), 6.7–8.2- (complex m, 26H).

EXAMPLE 16

Using an analogous procedure to that described in Example 1, but starting from 2-ethyl-6-(1-hydroxy-2-propoxy)-4-[(2'-(2-triphenylmethyl-2H-tetrazol-5-yl)biphenyl-4-yl)methoxy]-1,5-naphthyridine (A), there was obtained in 30% yield 2-ethyl-6-(1-hydroxy-2-propoxy)-4-[(2'-(1H-tetrazol-5-yl)biphenyl-4-yl)methoxy]-1,5-naphthyridine hydrochloride, m.p. 183°–189° C.; mass spectrum (+ve FAB, DMSO/N-BA/CHCl$_3$): 483(M+H)$^+$; microanalysis, found: C, 61.1; H, 5.2; N, 15.8; Cl, 6.2; H$_2$O, 3.1%; C$_{27}$H$_{26}$N$_6$O$_3$.HCl.0.8H$_2$O requires: C, 60.7; H, 5.4; N, 15.7; Cl, 6.6; H$_2$O, 2.7%.

The starting material (A) was obtained as follows:

A solution of 6-[1-(ethoxycarbonyl)ethoxy]-2-ethyl-4-[(2'-(2-triphenylmethyl-2H-tetrazol-5-yl)biphenyl-4-yl)methoxy]-1,5-naphthyridine (1.0 g) in THF (8 ml) was added to a stirred suspension of lithium aluminium hydride (100 mg) in THF (5 ml) at 0° C. The mixture was allowed to warm to ambient temperature and then stirred for 20 hours. Water (0.1 ml), 15% w/v sodium hydroxide solution (0.1 ml) and water (0.3 ml) were added and the mixture was stirred for 30 minutes. The insoluble solid was removed by filtration and the filtrate was concentrated by evaporation. The residue was triturated with ether to give 2-ethyl-6-(1-hydroxy-2-propoxy)-4-[(2'-(2-triphenylmethyl-2H-tetrazol-5-yl)biphenyl-4-yl)methoxy]-1,5-naphthyridine (A) (0.89 g), m.p. 146°–150° C.; NMR (d$_6$-DMSO); 1.25–1.35(m, 6H), 2.8(q, 2H), 3.35–3.45(m, 1H), 3.6(s, 2H), 5.4(s, 2H), 6.8–6.9(m, 6H), 7.05–7.15(m, 3H), 7.2–7.4(m, 10H), 7.45–7.6(m, 5H), 7.8(dd, 1H), 8.1(d, 1H).

EXAMPLE 17

Using an analogous procedure to that described in Example 1, but starting from 2-ethyl-6-(4-fluorophenoxy)-4-[(2'-(2-triphenylmethyl-2H-tetrazol-5-yl)biphenyl-4-yl)methoxy]-1,5-naphthyridine (A), there was obtained in 47% yield 2-ethyl-6-(4-fluorophenoxy)-4-[(2'-(1H-tetrazol-5-yl)biphenyl-4-yl)methoxy]-1,5-naphthyridine hydrochloride, m.p. 212°–214° C.; NMR (d$_6$-DMSO+d$_4$-acetic acid): 1.4(t, 3H), 3.2(q, 2H), 5.5(s, 2H), 7.1–7.3(m, 8H), 7.5–7.7(m, 6H), 8.6(d, 1H); mass spectrum (+ve FAB, DMSO/NBA): 519(M+H)$^+$; microanalysis, found: C, 64.5; H, 4.3; N, 15.0; Cl, 6.0%; C$_{30}$H$_{23}$FN$_6$O$_2$.HCl requires: C, 64.9; H, 4.4; N, 15.1; Cl, 6.4%.

The starting material (A) was obtained as follows:

(i) Using an analogous procedure to that described in Example 1, part (ii), but starting from 2-(4-fluorophenoxy)-5-nitropyridine (obtained as described in *J. Med. Chem.*, 1970, 7, 1219), there was obtained in 95% yield 5-amino-2-(4-fluorophenoxy)pyridine (B) as an oil; NMR (d$_6$-DMSO): 6.7(d, 1H), 6.9–7.1(m, 5H), 7.5(s, 1H).

(ii) Using an analogous procedure to that described in Example 1, part (iii), but starting from compound B, there was obtained in 74% yield 2-ethyl-6-(4-fluorophenoxy)-1,5-naphthyridine-4(1H)-one (C), m.p. >250° C.; NMR (d$_6$-DMSO): 1.2(t, 3H), 2.5(q, 2H), 6.1(s, 2H), 7.2(d, 4H), 7.4(d, 1H), 8.0(d, 1H).

(iii) Using an analogous procedure to that described in Example 1, part (iv), but starting from compound B, there was obtained in 64% yield 2-ethyl-6-(4-fluorophenoxy)-4-[(2'-(2-triphenylmethyl-2H-tetrazol-5-yl)biphenyl-4-yl)methoxy]-1,5-naphthyridine (A), m.p. 167°–172° C.; NMR (CDCl$_3$): 1.4(t, 3H), 2.9(q, 2H), 5.2(s, 2H), 6.9–7.5(m, 28H), 7.9(d, 1H), 8.3(d, 1H).

EXAMPLE 18

Using an analogous procedure to that described in Example 1, but starting from 2-ethyl-6-(3-pyridyloxy)-4-[(2'-(2-triphenylmethyl-2H-tetrazol-5-yl)biphenyl-4-yl)methoxy]-1,5-naphthyridine (A), there was obtained in 39% yield 2-ethyl-6-(3-pyridyloxy)-4-[(2'-(1H-tetrazol-5-yl)biphenyl-4-yl)methoxy]-1,5-naphthyridine dihydrochloride, m.p. 197°–204° C.; NMR (d$_6$-DMSO+d$_4$-acetic acid): 1.5(t, 3H), 3.2(q, 2H), 5.5(s, 2H), 7.2–7.4(m, 4H), 7.6–7.8(m, 5H), 7.95–8.05(m, 2H), 8.5(d, 1H), 8.8(d, 2H), 9.0(d, 1H); microanalysis, found: C, 56.8; H, 4.7; N, 15.6; Cl, 11.6; H$_2$O, 7.0%; C$_{29}$H$_{23}$N$_7$O$_2$.2HCl.2.5H$_2$O requires: C, 56.4; H, 4.9; N, 15.9; Cl, 11.5; H$_2$O, 7.3%.

The starting material (A) was obtained as follows:

(i) A mixture of 2-chloro-5-nitropyridine (7 g), 3-hydroxypyridine (4.2 g) and potassium hydroxide (2.47 g) in ethanol (70 ml) was heated under reflux for 3 hours. Volatile material was removed by evaporation and the residue was partitioned between water (200 ml) and ethyl acetate (200 ml). The organic phase was separated, washed with saturated sodium chloride solution (200 ml) and dried (MgSO$_4$). The solvent was removed by evaporation and the residue triturated with ether to give 5-nitro-2-(3-pyridyloxy)pyridine (B) (5.9 g), m.p. 85°–88° C.; NMR (d$_6$-DMSO): 7.4(d, 1H), 7.45–7.55(m, 1H), 7.75–7.85(m, 1H), 8.45–8.55(m, 2H), 8.7(dd, 1H), 9.0(d, 1H).

(ii) Using an analogous procedure to that described in Example 1, part (ii), but starting from compound B, there was obtained in 99% yield 5-amino-2-(3-pyridyloxy)pyridine (C) as an oil; NMR (d$_6$-DMSO); 5.1(br s, 2H), 6.9(d, 1H), 7.3–7.6(m, 4H), 8.3–8.5(m, 2H).

(iii) Using an analogous procedure to that described in Example 1, part (iii), but starting from compound C, there was obtained in 41% yield 2-ethyl-6-(3-pyridyloxy)-1,5-naphthyridin-4(1H)-one (D), m.p. 247°–250° C.; NMR (d$_6$-DMSO): 1.2(t, 3H), 2.6(q, 2H), 6.0(s, 1H), 7.0(d, 1H), 7.35–7.45(m, 1H), 7.65–7.75(m, 1H), 8.1(d, 1H), 8.5(d, 1H), 8.55(dd, 1H), 11.6(br s, 1H).

(iv) Using an analogous procedure to that described in Example 1, part (iv), but starting from compound D, there was obtained in 54% yield 2-ethyl-6-(3-pyridyloxy)-4-[(2'-(2-triphenylmethyl-2H-tetrazol-5-yl)biphenyl-4-yl)methoxy]-1,5-naphthyridine (A), m.p. 155°–160° C.; NMR (d$_6$-DMSO+d$_4$-acetic acid): 1.4(t, 3H), 3.0(q, 2H), 5.3(s, 2H), 6.7–6.9(m, 6H), 7.1(d, 2H), 7.3–7.7(m, 17H), 7.9(dd, 2H), 8.3–8.5(m, 2H), 8.65(s, 1H).

EXAMPLE 19

A mixture of 6-(2-aminoethoxy)-2-ethyl-4-[(2'-(2-triphenylmethyl-2H-tetrazol-5-yl)biphenyl-4-yl)methoxy]quinoline (A) (680 mg), methanol (7 ml) and 11M hydrochloric acid (0.7 ml) was stirred for 4 hours. Volatile material was removed by evaporation and the residue was triturated with ether (50 ml) The ether was decanted off and the solid residue was retriturated with dimethoxyethane (50 ml) and then with ethyl acetate (50 ml) to give 6-(2-aminoethoxy)-2-ethyl-4-[(2'-(1H-tetrazol-5-yl)biphenyl-4-yl)methoxy]quinoline dihydrochloride (420 mg), as an amorphous powder, m.p. 163°-172° C. (dec); NMR ($d_6$-DMSO): 1.45(t, 3H), 3.18(q, 2H), 3.39(t, 2H), 4.42(t, 2H), 5.68(s, 2H), 7.25(d, 2H), 7.50-7.85(m, 9H), 8.25(d, 1H); mass spectrum [−ve FAB, DMSO/GLYCEROL]: 465 (M−H)−.

The starting material (A) was obtained as follows:

(i) Sodium hydride (60% dispersion in mineral oil; 2 g) was added to a stirred solution of 4-nitrophenol (7 g) in DMF (100 ml) cooled in an ice-water bath. The mixture was stirred until evolution of hydrogen had ceased and N-(2-bromoethyl)phthalimide (12.6 g) was then added. The mixture was stirred and heated at reflux for 10 hours. The cooled mixture was then added to ice-water (500 ml). The precipitated solid was collected by filtration, washed with water and recrystallised from 95% ethanol to give N-(2-(4-nitrophenoxy)ethyl)phthalimide (9.9 g), as crystalline solid, m.p. 151°-153° C.; NMR 4.15(t, 2H), 4.35(t, 2H), 6.95(m, 2H), 7.74(m, 2H), 7.88(m, 2H), 8.18(m, 2H).

(ii) Platinum oxide (54 mg) was added to a solution of N-(2-(4-nitrophenoxy)ethyl)phthalimide (5.1 g) in DMF (70 ml) and the mixture was hydrogenated at 1 atmosphere pressure until the uptake of hydrogen ceased. The catalyst was filtered off through diatomaceous earth and the filtrate was evaporated. Water (50 ml) was added to the residue and the mixture was left to stand for 18 hours. The water was decanted to leave a solid residue. The solid residue was triturated with ethanol and collected by filtration to give. N-(2-(4-aminophenoxy)ethyl)phthalimide (4.4 g), which was used without further purification or characterisation.

(iii) A mixture of N-(2-(4-aminophenoxy)ethyl)phthalimide (4.2 g), methylpropionylacetate (1.94 g) and p-toluenesulphonic acid (100 mg) in benzene (95 ml) was stirred and heated at reflux for 3 hours with azeotropic removal of water. Volatile material was then removed by evaporation and the residue was added to a refluxing eutectic mixture of 26.5% v/v diphenyl and 73.5% v/v diphenyl oxide (25 ml). The mixture was heated at reflux for 15 minutes and then cooled to ambient temperature. Hexane (80 ml) was added to the mixture which was triturated to give a solid. The solid was collected by filtration and washed with hexane. Ethyl acetate (70 ml) was added to the solid and the mixture was heated at reflux for 5 minutes and then cooled in an ice-bath. The undissolved solid was collected by filtration and washed with ethyl acetate to give 2-ethyl-6-(2-phthalimidoethoxy)-4-quinolone (2.5 g) as an off white solid, m.p. 168°-171° C.; NMR ($d_6$-DMSO): 1.24(t, 3H), 2.59(q, 2H), 4.0(t, 2H), 4.28(t, 2H), 5.87(s, 1H), 7.18(dd, 1H), 7.45(m, 2H), 7.84(m, 4H), 11.4(br s, 1H).

(iv) Sodium hydride (60% dispersion in mineral oil; 120 mg) was added to a stirred mixture of 2-ethyl-6-(2-phthalimidoethoxy)-4-quinolone (1 g) of DMF (30 ml). The mixture was stirred until evolution of hydrogen had ceased and then a solution of 5-[2-(4'-bromomethylbiphenylyl)]-2-triphenylmethyl-2H tetrazole (1.8 g) in DMF (7.5 ml) was added. The mixture was stirred for 18 hours. The solvent was removed by evaporation and the residue partitioned between water (50 ml) and dichloromethane (150 ml). The organic layer was washed with saturated sodium chloride solution (20 ml) and dried ($MgSO_4$). The solvent was removed by evaporation and the residue was purified by flash chromatography eluting with methanol/ethyl acetate/dichloromethane (1:10:89 v/v) to give 2-ethyl-6-(2-phthalimidoethoxy)-4-[(2'-(2-triphenylmethyl-2H-tetrazol-5-yl)biphenyl-4-yl)methoxy]quinoline (1.0 g) as a foam; NMR ($d_6$-DMSO): 1.28(t, 3H), 2.81(q, 2H), 3.99(t, 2H), 4.28(t, 2H), 5.35(s, 2H), 6.8-6.94(m, 6H), 7.0(s, 1H), 7.15(d, 2H), 7.25-7.38(m, 10H), 7.42(d, 2H), 7.45-7.7(m, 4H), 7.75-7.9(m, 6H).

(v) A mixture of 2-ethyl-6-(2-phthalimidoethoxy)-4-[(2'-(2-triphenylmethyl-2H-tetrazole-5-yl)biphenyl-4-yl)methoxy]quinoline (900 mg), a solution of methylamine in industrial methylated spirits (33% w/v; 9 ml) and water (0.9 ml) was stirred for 1 hour. Water (8.1 ml) was added and the mixture was stirred for a further 10 minutes. The precipitated solid was collected by filtration and washed with 50% aqueous ethanol (4 ml). The solid was then dried over phosphorous pentoxide to give 6-aminoethoxy-2-ethyl-4-[(2'-(2-triphenylmethyl-2H-tetrazol-5-yl)biphenyl-4-yl)methoxy]quinoline (A) (698 mg); NMR ($d_6$-DMSO): 1.29(t, 3H), 2.83(q, 2H), 2.9(t, 2H), 3.95(t, 2H), 5.34(s, 2H), 6.80-6.85(m, 6H), 7.02(s, 1H), 7.15(d, 2H), 7.40-7.70(m, 15H), 7.82(m, 2H).

EXAMPLE 20

Pharmaceutical dosage forms, suitable for presenting the compounds of the invention for therapeutic or prophylactic use, include conventional tablet, capsule, injection and aersol formulations. The following illustrative formulations may be obtained by conventional procedures well known in the art of pharmacy and are suitable for therapeutic or prophylactic use in humans:

| Tablet I | mg/tablet |
| --- | --- |
| Compound Z* | 5.0 |
| Lactose Ph. Eur. | 89.25 |
| Croscarmellose sodium | 4.0 |
| Maize starch paste (5% w/v aqueous paste) | 0.75 |
| Magnesium stearate | 1.0 |

| Tablet II | mg/tablet |
| --- | --- |
| Compound Z* | 50 |
| Lactose Ph. Eur | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |

| Tablet III | mg/tablet |
| --- | --- |
| Compound Z* | 100 |
| Lactose Ph. Eur. | 182.75 |
| Croscarmellose sodium | 12.0 |
| Maize starch paste (5% w/v aqueous paste) | 2.25 |
| Magnesium stearate | 3.0 |

| Capsule | mg/capsule |
| --- | --- |
| Compound Z* | 10 |
| Lactose Ph. Eur. | 488.5 |

| Capsule | mg/capsule |
|---|---|
| Magnesium stearate | 1.5 |
Note:
compound Z* may be a compound of formula I such as one of the previously described specific examples herein or a physiologically acceptable salt thereof.
CHEMICAL FORMULAE
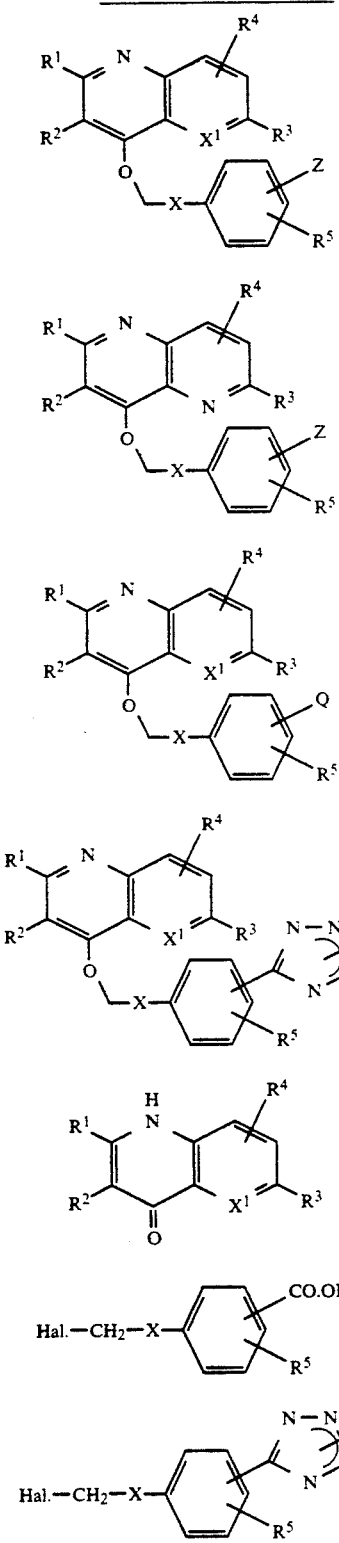
-continued
CHEMICAL FORMULAE

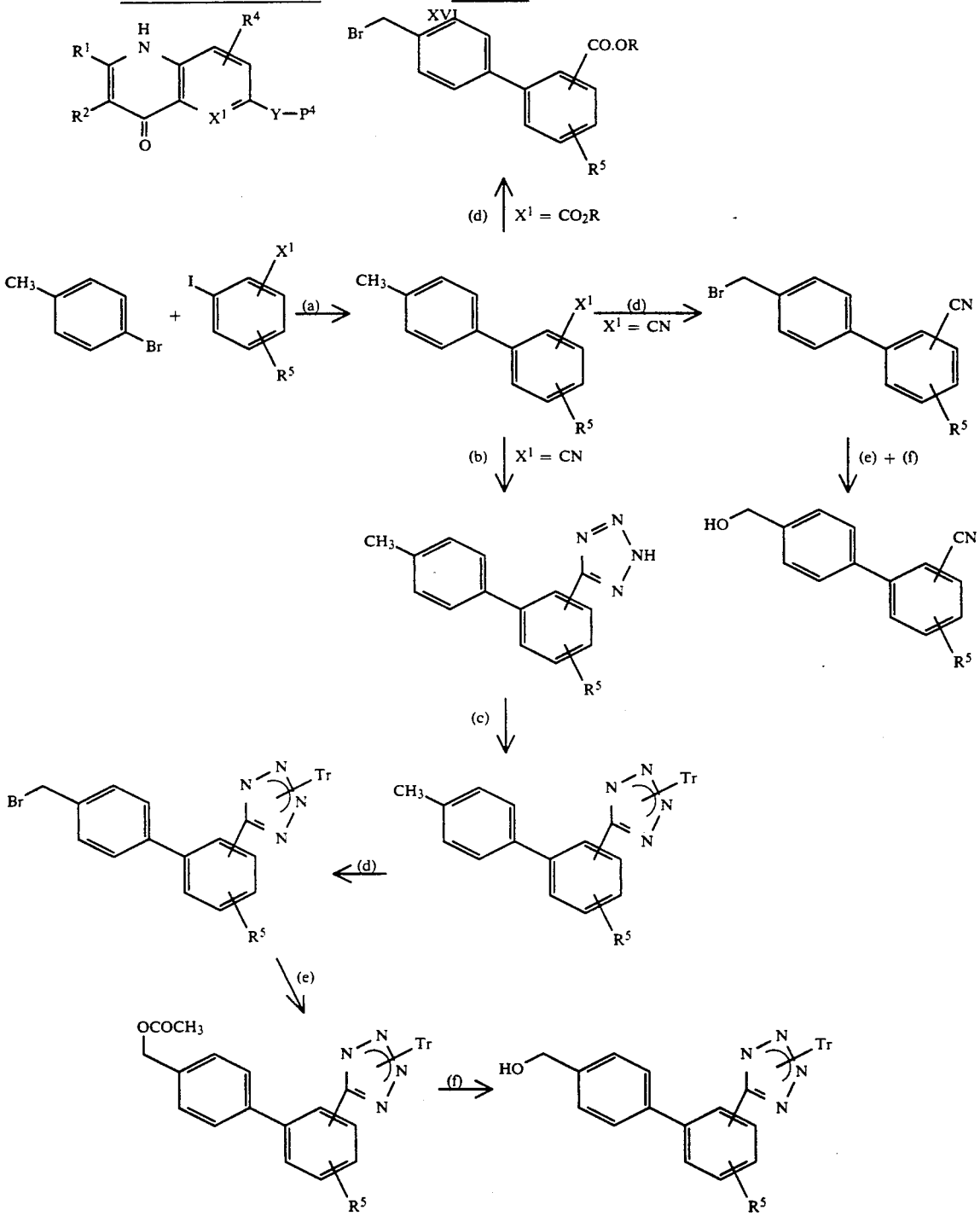
Note: R = lower alkyl, benzyl, phenyl; Tr = triphenylmethyl (trityl)

Reagents: a) BuLi/THF; ZnCl$_2$/Et$_2$O; Pd(Ph$_3$P)$_4$
b) Bu$_3$Sn.N$_3$/toluene; HCl/toluene
c) Tr.Cl/Et$_3$N/CH$_2$Cl$_2$
d) N-bromosuccinimide/azoisobutyronitrile/CCl$_4$
e) Potassium acetate, hexaoxacyclooctadecane, DME, reflux
f) Lithium borohydride, THF, 0-25° C.

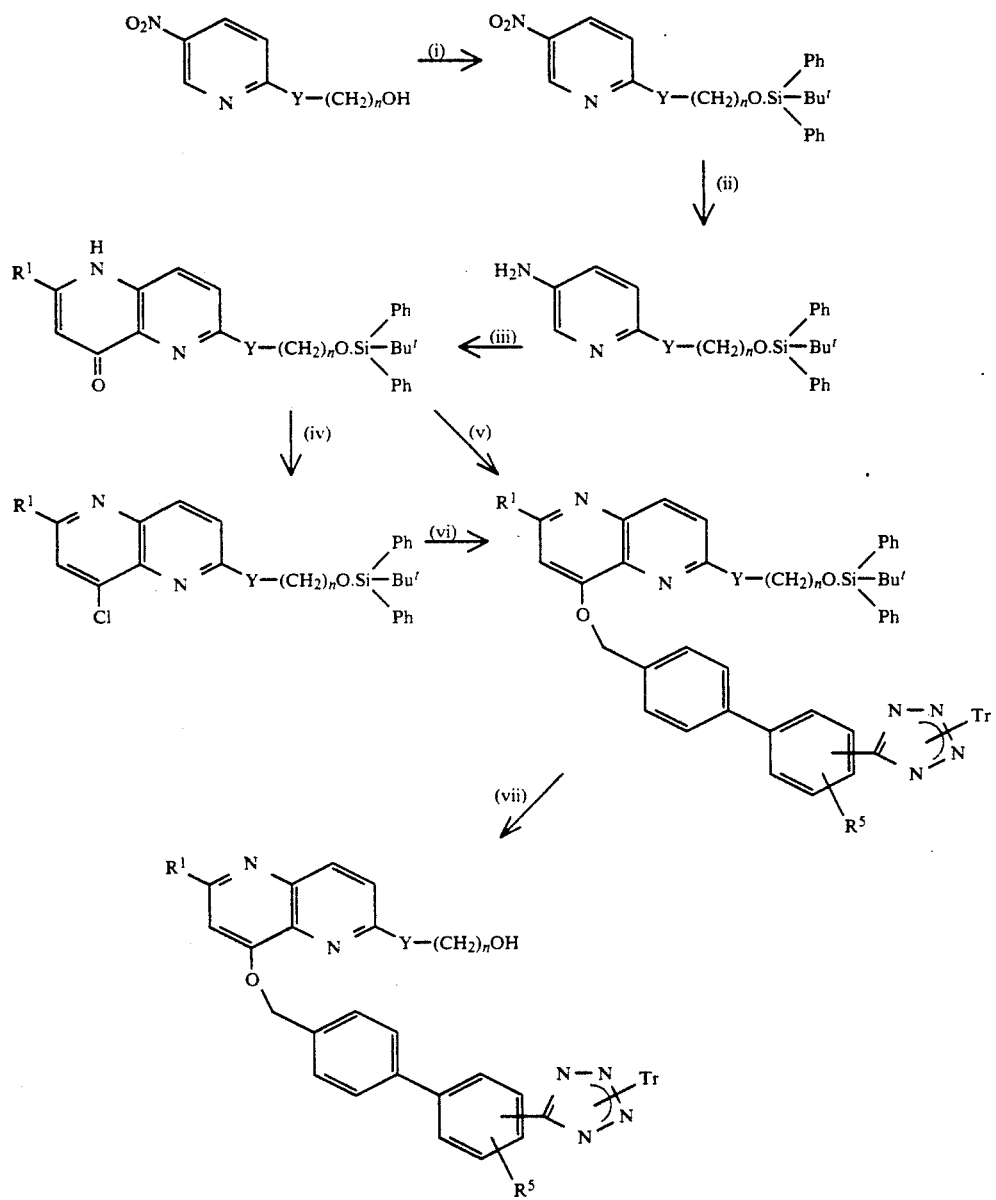

Scheme 2

Note: n = 1-6; Tr = triphenylmethyl (trityl); Y = oxygen or sulphur
Reagents: (i) tert-butylchlorodiphenylsilane, NaH, DMF, 0-10° C.
(ii) Hydrogenation over Pd/C
(iii) R$^1$.CO.CH$_2$.CO$_2$CH$_3$, PTSA, cyclohexane; then heat at 260° C.
(iv) POCL$_3$, toluene or dioxane, reflux
(v) Formula VI compound (X = p-phenylene, L = trityl), NaH, DMF
(vi) Formula XII compound (X = p-phenylene, L = trityl), NaH, DMF
(vii) Tetrabutylammonium fluoride, THF

What we claim is:
1. A compound of the formula I

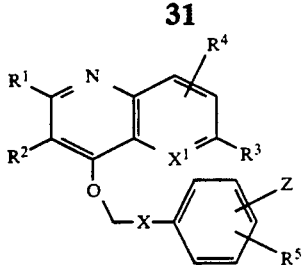

wherein:
R¹ is hydrogen, (1–8C)alkyl, (3–8C)cycloalkyl, (3–8C)cycloalkyl(1–4C)alkyl, phenyl, phenyl(1–4C)alkyl or (1–4C)alkyl bearing one or more fluoro substituents;

R² is hydrogen or (1–4C)alkyl;

R³ is phenyloxy, pyridyloxy or a group of the formula -Y.A.B. wherein Y is an oxygen or sulphur atom; A is (1–6C)alkylene, (3–6C)alkenylene or a 1,3-cyclopentylene or 1,4-cyclohexylene moiety, the latter two groups optionally bearing 1 or 2 (1–4C)alkyl groups; and B is selected from hydroxy, (1–4C)alkoxy, phenyl, phenyloxy, phenyl(1–4C)alkoxy, pyridyl(1–4C)alkoxy, 4-morpholino(1–4C)alkoxy, phenylamino, amino, alkylamino and dialkylamino of up to 6 carbon atoms, (1–4C)alkanoylamino, (1–4C)alkylsulphonylamino, phenylsulphonylamino, sulphamoylamino (—NH.SO₂.NH₂), carboxamidomethylamino (—NH.CH₂.CO.NH₂), (1–4C)alkanoyloxy, phenylcarbonyloxy, aminocarbonyloxy (—O.CO.NH₂), (1–4C)alkylaminocarbonyloxy, carboxy, (1–4C)alkoxycarbonyl, carbamoyl, N-alkylcarbamoyl and di-(N-alkyl)carbamoyl of up to 7 carbon atoms, (1–4C)alkanoyl, 4-morpholino, 1-imidazolyl, succinimido, thiazolyl and thiadiazolyl; or B is a group of the formula —Y¹.B¹. wherein Y¹ is oxy, oxycarbonyl or imino and B¹ is a 5 or 6-membered saturated or unsaturated heterocyclic ring containing 1 or 2 nitrogen atoms and linked to Y¹ by a ring carbon atom; or Y¹ is oxycarbonyl and B¹ is a 4-morpholino group or a 5 or 6-membered saturated heterocyclic ring containing 1 or 2 nitrogen atoms, optionally bearing a (1–4C)alkyl group and linked to Y¹ by a ring nitrogen atom; and wherein in B¹ the remainder of the ring atoms are carbon;

R⁴ is selected from hydrogen, (1–4C)alkyl, (1–4C)alkoxy, fluoro(1–4C)alkoxy, halogeno, trifluoromethyl, cyano, nitro, hydroxy, amino, alkylamino and dialkylamino of up to 6 carbon atoms, carboxy, (1–4C)alkoxycarbonyl, carbamoyl and N-alkylcarbamoyl and di-(N-alkyl)carbamoyl of up to 7 carbon atoms;

R⁵ is hydrogen, (1–4C)alkyl, (1–4C)alkoxy, halogeno, trifluoromethyl, cyano or nitro;

X is phenylene optionally bearing a substituent selected from (1–4C)alkyl, (1–4C)alkoxy, halogeno, trifluoromethyl, cyano and nitro, or X is a direct bond between the adjacent phenyl and methylene groups;

X¹ is a methine (—CH=) group or a nitrogen atom; and

Z is 1H-tetrazol-5-yl, —CO.NH.(1H-tetrazol-5-yl) or a group of the formula —CO.OR⁶ or —CO.NH.SO₂.R⁷ in which R⁶ is hydrogen or a non-toxic, biodegradable residue of a physiologically acceptable alcohol or phenol, and R⁷ is (1–6C)alkyl, (3–8C)cycloalkyl or phenyl; and wherein any of said phenyl moieties may be unsubstituted or bear one or two substituents independently selected from (1–4C)alkyl, (1–4C)alkoxy, halogeno, cyano and trifluoromethyl; or a physiologically acceptable salt thereof.

2. A compound as claimed in claim 1 wherein

R¹ is hydrogen, methyl, ethyl, propyl, butyl, isobutyl, sec-butyl, pentyl, hexyl, cyclopropyl, cyclopentyl, cyclohexyl, cyclopropylmethyl, cyclopentylmethyl, cyclohexylmethyl, 2-cyclopentyl-ethyl, phenyl, benzyl, 1-phenylethyl, 2-phenylethyl, fluoromethyl, trifluoromethyl, 2,2,2-trifluoroethyl or pentafluoroethyl;

R² is hydrogen, methyl or ethyl;

R³ is phenyloxy, pyridyloxy or a group of the formula -Y.A.B wherein

Y is an oxygen or sulphur atom;

A is a methylene, ethylene, trimethylene or tetramethylene group, in any of which last four groups one methylene may bear 1 or 2 methyl substituents, or A is a —CH₂.CH=CH— or —CH₂.CH=CH.CH²— group; and B is hydroxy, methoxy, ethoxy, isopropoxy, phenyl, phenyloxy, benzyloxy, phenethyloxy, 2-pyridylmethoxy, 3-pyridylmethoxy, 4-pyridylmethoxy, 3-pyridylethoxy, 4-morpholinomethoxy, 4-morpholinoethoxy, phenylamino, amino, methylamino, ethylamino, butylamino, dimethylamino, diethylamino, dipropylamino, formamido, acetamido, propionylamido, methylsulphonylamino, ethylsulphonylamino, phenylsulphonylamino, sulphamoylamino, carboxamidomethylamino, acetyloxy, propionyloxy, phenylcarbonyloxy, aminocarbonyloxy, methylaminocarbonyloxy, ethylaminocarbonyloxy, carboxy, methoxycarbonyl, ethoxycarbonyl, propoxycarbonyl, carbamoyl, N-methylcarbamoyl, N-ethylcarbamoyl, N,N-dimethylcarbamoyl, N,N-diethylcarbamoyl, formyl, acetyl, propionyl, 4-morpholino, 1-imidazolyl, succinimido, thiazolyl or thiadiazolyl; or B is a group of the formula —Y¹.B¹ wherein Y¹ is oxy, oxycarbonyl or imino and B¹ is pyrrolidinyl, imidazolidinyl, pyrazolinyl, piperidinyl, piperazinyl, pyrrolyl, imidazolyl, pyrazolyl, pyridyl, pyrazinyl, pyrimidinyl or pyridazinyl linked to Y¹ by a ring carbon atom; or Y¹ is oxycarbonyl and B¹ is 4-morpholino, pyrrolidinyl, imidazolidinyl, pyrazolinyl, piperidinyl or piperazinyl and is linked to Y¹ by a ring nitrogen atom;

R⁴ is selected from hydrogen, methyl, ethyl, methoxy, ethoxy, isopropoxy, trifluoromethoxy, 2-fluoroethoxy, 2,2,2-trifluoroethoxy, 3,3,3-trifluoropropoxy, fluoro, chloro, bromo, iodo, trifluoromethyl, cyano, nitro, hydroxy, amino, methylamino, ethylamino, butylamino, dimethylamino, diethylamino, dipropylamino, carboxy, methoxycarbonyl, ethoxycarbonyl, propoxycarbonyl, carbamoyl, N-methylcarbamoyl, N-ethylcarbamoyl, N,N-dimethylcarbamoyl and N,N-diethylcarbamoyl;

R⁵ is hydrogen, methyl, ethyl, methoxy, ethoxy, isopropoxy, fluoro, chloro, bromo, iodo, trifluoromethyl, cyano or nitro;

X is phenylene optionally bearing a substituent selected from methyl, ethyl, methoxy, ethoxy, isopropoxy, fluoro, chloro, bromo, iodo, trifluoromethyl, cyano and nitro, or X is a direct bond between the adjacent phenyl and methylene groups;

R⁶ is hydrogen or a residue derived from a (1-6C)alkanol, or phenol or glycerol; and R⁷ is methyl, ethyl, propyl, isopropyl, butyl, pentyl, cyclobutyl, cyclopentyl, cyclohexyl or phenyl; and wherein any of said phenyl moieties may be unsubstituted or bear one or two substituents independently selected from methyl, ethyl, methoxy, ethoxy, fluoro, chloro, bromo, cyano and trifluoromethyl.

3. A compound as claimed in claim 1 wherein R³ is a group of the formula —Y.A.B wherein Y is an oxygen or sulphur atom; A is (1-6C)alkylene, (3-6C)alkenylene or a 1,3-cyclopentylene or 1,4-cyclohexylene moiety, the latter two groups optionally bearing 1 or 2 (1-4C)alkyl groups; and B is selected from hydroxy, (1-4C)alkoxy, phenyloxy, phenyl(1-4C)alkoxy, pyridyl(1-4C)alkoxy, 4-morpholino(1-4C)alkoxy, phenylamino, amino, alkylamino and dialkylamino of up to 6 carbon atoms, (1-4C)alkanoylamino, (1-4C)alkylsulphonylamino, phenylsulphonylamino, sulphamoylamino (—NH.SO₂.NH₂), carboxamidomethylamino (—NH.CH₂.CO.NH₂), (1-4C)alkanoyloxy, phenylcarbonyloxy, aminocarbonyloxy (—O.CO.NH₂), (1-4C)alkylaminocarbonyloxy, carboxy, (1-4C)alkoxycarbonyl, carbamoyl, N-alkylcarbamoyl and di-(N-alkyl)carbamoyl of up to 7 carbon atoms, (1-4C)alkanoyl, 4-morpholino, 1-imidazolyl and succinimido; or B is a group of the formula —Y¹.B¹. wherein Y¹ is oxy, oxycarbonyl or imino and B¹ is a 5 or 6-membered saturated or unsaturated heterocyclic ring containing 1 or 2 nitrogen atoms and linked to Y¹ by a ring carbon atom; or Y¹ is oxycarbonyl and B¹ is a 4-morpholino group or a 5 or 6-membered saturated heterocyclic ring containing 1 or 2 nitrogen atoms, optionally bearing a (1-4C)alkyl group and linked to Y¹ by a ring nitrogen atom; and wherein in B¹ the remainder of the ring atoms are carbon.

4. A naphthyridine of the formula Ia

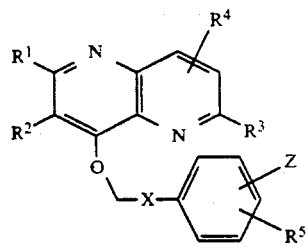

Ia wherein R¹, R², R³, R⁴, R⁵, X and Z have any of the meanings as defined in claim 1; or a physiologically acceptable salt thereof.

5. A naphthyridine of the formula Ia

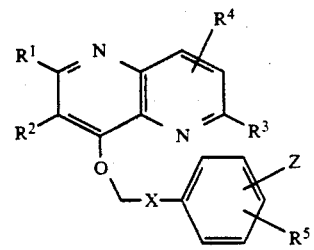

Ia wherein R¹, R², R³, R⁴, R⁵, X and Z have any of the meanings as defined in claim 2; or a physiologically acceptable salt thereof.

6. A naphthyridine of the formula Ia

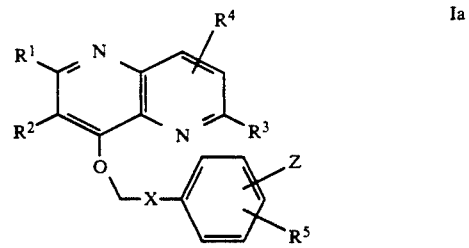

Ia wherein R¹, R², R³, R⁴, R⁵, X and Z have any of the meanings as defined in claim 3; or a physiologically acceptable salt thereof.

7. A compound as claimed in claim 1, 4, 5 or 6 wherein R³ is a group of the formula —Y.A.B wherein Y is oxygen, A is (1-6C)alkylene and B is hydroxy.

8. A compound as claimed in claim 1, 4, 5 or 6 wherein X is p-phenylene and Z is 1H-tetrazol-5-yl attached ortho to the group X.

9. A compound of the formula I selected from:
2-ethyl-6-(2-hydroxyethoxy)-4-[(2'-(1H-tetrazol-5-yl)biphenyl-4-yl)methoxy]-1,5-naphthyridine;
2-ethyl-6-(2-ethylaminocarbonyloxy)ethoxy)-4-[(2'-(1H-tetrazol-5-yl)biphenyl-4-yl)methoxy]-1,5-naphthyridine;
2-ethyl-6-(2-methoxyethoxy)-4-[(2'-(1H-tetrazol-5-yl)biphenyl-4-yl)methoxy]-1,5-naphthyridine;
2-ethyl-6-[2-(4-morpholinocarbonyloxy)ethoxy]-4-[(2'-(1H-tetrazol-5-yl)biphenyl-4-yl)methoxy]-1,5-naphthyridine;
6-(Aminocarbonylmethoxy)-2-ethyl-4-[(2'-(1H-tetrazol-5-yl)biphenyl-4-yl)methoxy]-1,5-naphthyridine;
6-[N,N-Diethylaminocarbonyl)methoxy]-2-ethyl-4-[(2'-(1H-tetrazol-5-yl)biphenyl-4-yl)methoxy]-1,5-naphthyridine;
2-Ethyl-4-[(2'-(1H-tetrazol-5-yl)biphenyl-4-yl)methoxy]-6-[(thiazol-4-yl)methoxy]-1,5-naphthyridine;
2-ethyl-6-(2-hydroxy-2-methyl-1-propoxy)-4-[(2'-(1H-tetrazol-5-yl)biphenyl-4-yl)methoxy]-1,5-naphthyridine;
6-(2-aminoethoxy)-2-ethyl-4[(2'-(1H-tetrazol-5-yl)biphenyl-4-yl)methoxy]quinoline;
and the physiologically acceptable salts thereof.

10. A salt as claimed in claim 1 which is selected from salts with acids forming physiologically acceptable anions and, for those compounds of formula I which are acidic, alkali metal, alkaline earth metal, aluminium amd ammonium salts, and salts with organic bases affording physiologically acceptable cations.

11. A method for antagonising one or more of the actions of angiotensin II in a warm-blooded animal requiring such treatment which comprises administering to said animal an antagonistically effective amount of a compound of formula I, or a non-toxic salt thereof, as defined in claim 1.

12. A pharmaceutical composition which comprises a compound of the formula I or Ia, or a physiologically acceptable salt thereof, as claimed in claim 1 or 4, together with a pharmaceutically acceptable diluent or carrier.

13. A compound of the formula III
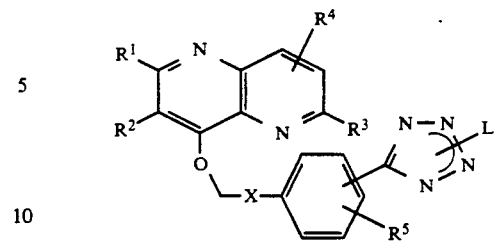
wherein $R^1$, $R^2$, $R^3$, $R^4$, $R^5$, X and $X^1$ have any of the meanings defined in claim 1, and L is a protecting group.
* * * * *